United States Patent
Maeda

(10) Patent No.: US 10,922,897 B2
(45) Date of Patent: Feb. 16, 2021

(54) MEDICAL INFORMATION PROCESSING APPARATUS, X-RAY DIAGNOSTIC SYSTEM, AND MEDICAL INFORMATION PROCESSING METHOD

(71) Applicant: CANON MEDICAL SYSTEMS CORPORATION, Otawara (JP)

(72) Inventor: Tatsuo Maeda, Nasushiobara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 23 days.

(21) Appl. No.: 16/245,275

(22) Filed: Jan. 11, 2019

(65) Prior Publication Data
US 2019/0221046 A1 Jul. 18, 2019

(30) Foreign Application Priority Data

Jan. 15, 2018 (JP) .............................. JP2018-004410
Jan. 9, 2019 (JP) .............................. JP2019-001703

(51) Int. Cl.
G06T 19/20 (2011.01)
A61B 6/00 (2006.01)

(52) U.S. Cl.
CPC ............ *G06T 19/20* (2013.01); *A61B 6/4452* (2013.01); *A61B 6/466* (2013.01); *A61B 6/5264* (2013.01); *A61B 6/4441* (2013.01); *G06T 2210/41* (2013.01); *G06T 2219/2016* (2013.01)

(58) Field of Classification Search
CPC ................. G06T 19/20; G06T 2210/41; G06T 2219/2016; A61B 6/4452; A61B 6/466; A61B 6/5264; A61B 6/4441
USPC .......................................................... 378/62
See application file for complete search history.

(56) References Cited

U.S. PATENT DOCUMENTS

| 7,267,482 | B2* | 9/2007 | Ohishi | A61B 6/4441 |
| | | | | 378/196 |
| 8,345,957 | B2* | 1/2013 | Sakaguchi | A61B 6/466 |
| | | | | 382/154 |
| 8,824,633 | B2* | 9/2014 | Ohishi | A61B 6/4464 |
| | | | | 378/92 |
| 9,339,250 | B2* | 5/2016 | Mukumoto | A61B 6/466 |
| 9,642,588 | B2* | 5/2017 | Goto | A61B 6/4035 |
| 9,807,361 | B2* | 10/2017 | Kato | H04N 13/122 |

(Continued)

FOREIGN PATENT DOCUMENTS

| JP | 2009-542283 | 12/2009 |
| JP | 2013-233413 | 11/2013 |
| JP | 2013-240630 | 12/2013 |

*Primary Examiner* — Taeho Jo
(74) *Attorney, Agent, or Firm* — Oblon, McClelland, Maier & Neustadt, L.L.P.

(57) ABSTRACT

A medical information processing apparatus according to an embodiment causes a display to display a three-dimensional medical image, receives an operation of rotating direction of the three-dimensional medical image on the display, creates a figure indicating, in a case the three-dimensional medical image is rotated through the rotating operation, whether a movable member of an X-ray diagnostic apparatus can reach a position corresponding to the direction of the three-dimensional medical image after the rotation, based on the direction of the three-dimensional medical image on the display before the rotation, and causes the display to further display the figure.

16 Claims, 12 Drawing Sheets

(56) References Cited

U.S. PATENT DOCUMENTS

| | | | | |
|---|---|---|---|---|
| 2007/0025508 A1* | 2/2007 | Ohishi | ............... | A61B 6/469 |
| | | | | 378/62 |
| 2009/0022271 A1* | 1/2009 | Ohishi | ............... | A61B 6/4464 |
| | | | | 378/19 |
| 2010/0014740 A1* | 1/2010 | Movassaghi | ............ | A61B 6/469 |
| | | | | 382/132 |
| 2011/0044525 A1* | 2/2011 | Ohishi | ............... | A61B 6/463 |
| | | | | 382/132 |
| 2012/0200560 A1* | 8/2012 | Masumoto | ............. | G06T 19/20 |
| | | | | 345/419 |
| 2013/0169640 A1* | 7/2013 | Sakuragi | ............... | G06T 15/20 |
| | | | | 345/424 |
| 2013/0266123 A1* | 10/2013 | Yoshida | ............... | A61B 6/12 |
| | | | | 378/98.5 |
| 2015/0262357 A1* | 9/2015 | Igarashi | ............... | A61B 6/5217 |
| | | | | 382/131 |
| 2015/0279120 A1* | 10/2015 | Sakuragi | ............... | G06T 19/003 |
| | | | | 382/103 |
| 2017/0367673 A1* | 12/2017 | Ohishi | ............... | A61B 6/5217 |

* cited by examiner

POINTER

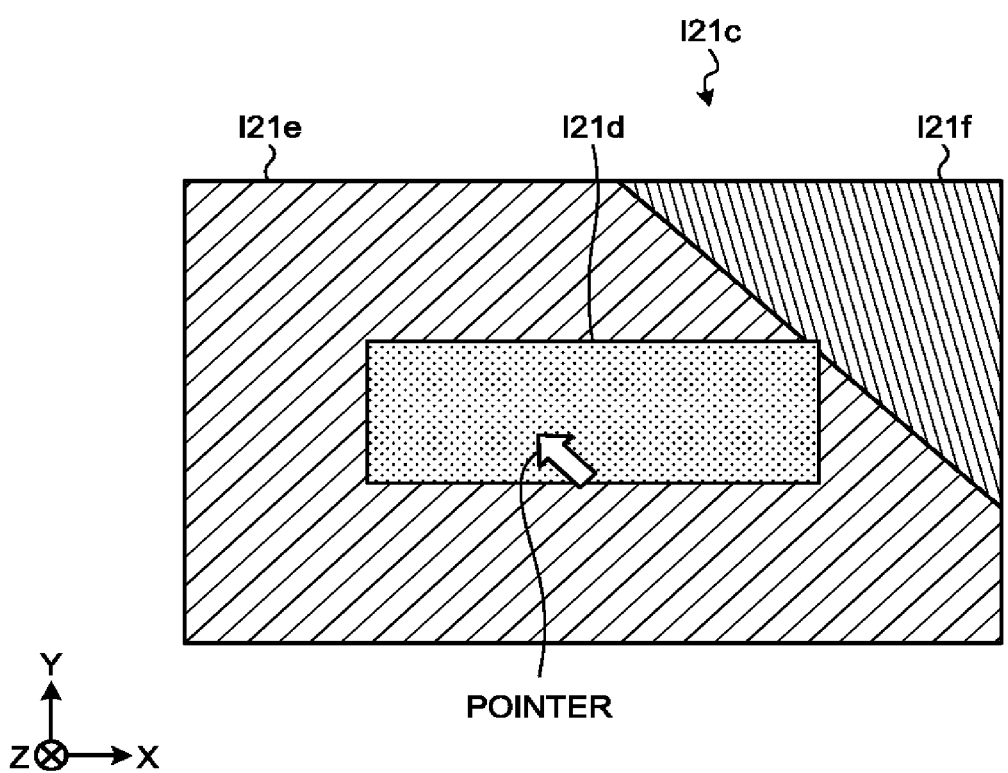

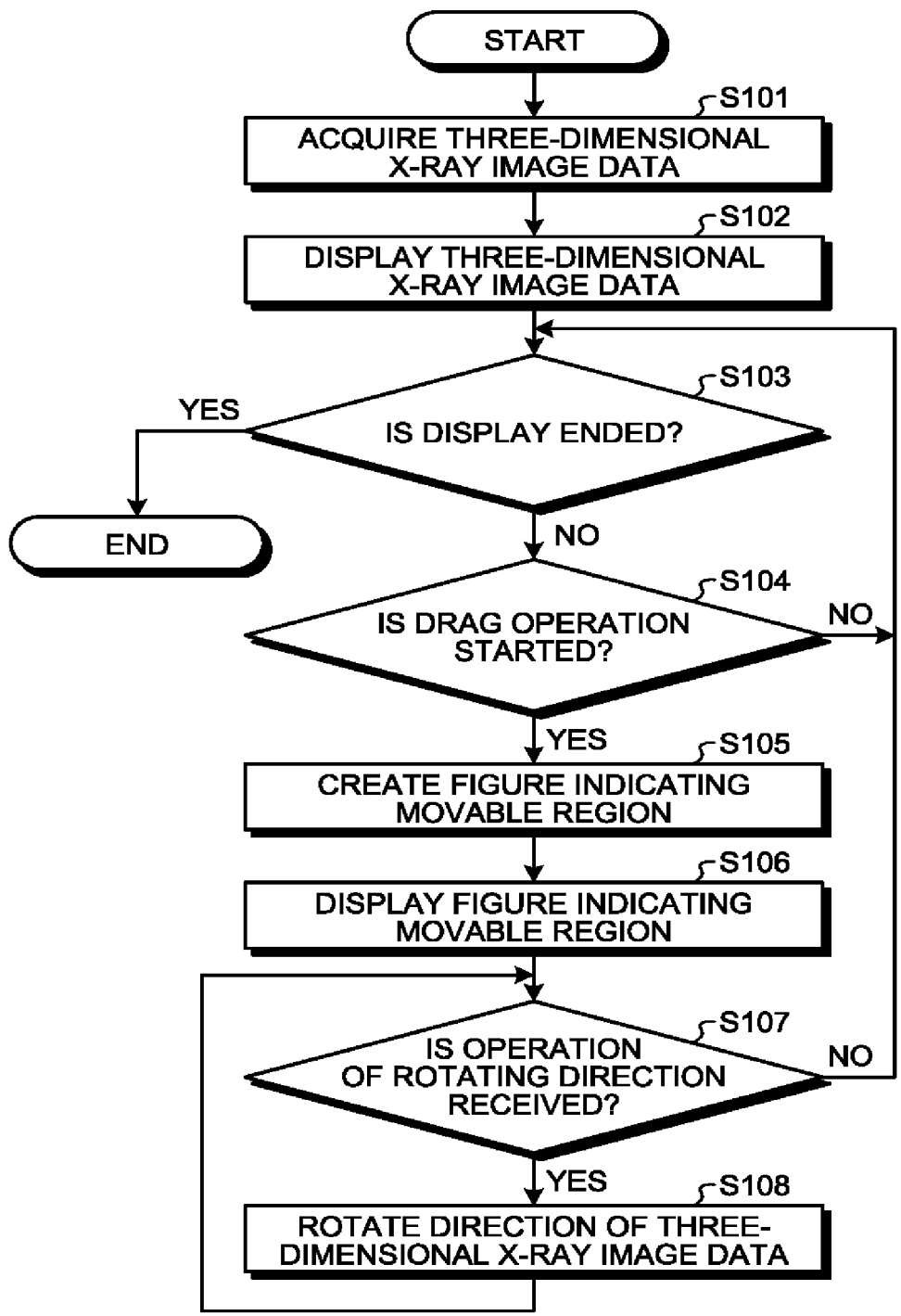

MEDICAL INFORMATION PROCESSING APPARATUS, X-RAY DIAGNOSTIC SYSTEM, AND MEDICAL INFORMATION PROCESSING METHOD

CROSS-REFERENCE TO RELATED APPLICATIONS

This application is based upon and claims the benefit of priority from Japanese Patent Application No. 2018-4410, filed on Jan. 15, 2018; and Japanese Patent Application No. 2019-1703, filed on Jan. 9, 2019, the entire contents of which are incorporated herein by reference.

FIELD

Embodiments described herein relate generally to a medical information processing apparatus, an X-ray diagnostic system, and a medical information processing method.

BACKGROUND

In intravascular treatment and the like, X-ray image data of a target region is displayed in real time for supporting surgery in some cases. In such a case, direction of X-rays to be emitted is set to easily observe the target region before surgery, the X-rays used for acquiring the X-ray image data to be displayed in real time. For example, in setting the direction of X-rays to be emitted, first, three-dimensional medical image data indicating the target region is acquired. An operator then selects direction with which the target region can be easily observed while rotating the three-dimensional medical image data, and sets the selected direction as the direction of X-rays to be emitted, the X-rays used for acquiring the X-ray image data to be displayed in real time.

BRIEF DESCRIPTION OF THE DRAWINGS

FIG. 7 is a diagram illustrating an example of a figure indicating the movable region of the movable member according to the first embodiment;

FIG. 8 is a flowchart for explaining a series of procedures of processing performed by a medical information processing apparatus according to the first embodiment;

DETAILED DESCRIPTION

A medical information processing apparatus according to an embodiment causes a display to display a three-dimensional medical image, receives an operation of rotating direction of the three-dimensional medical image on the display, creates a figure indicating whether a movable member of an X-ray diagnostic apparatus can reach a position corresponding to the rotated direction of the three-dimensional medical image in a case of rotating the three-dimensional medical image by the rotating operation based on the direction of the three-dimensional medical image on the display before being rotated, and causes the display to further display the figure.

The following describes embodiments of a medical information processing apparatus, an X-ray diagnostic system, and a medical information processing method in detail with reference to the drawings.

First, the following describes a first embodiment. The first embodiment describes, as an example, an X-ray diagnostic system including a medical information processing apparatus.

Figure 1:
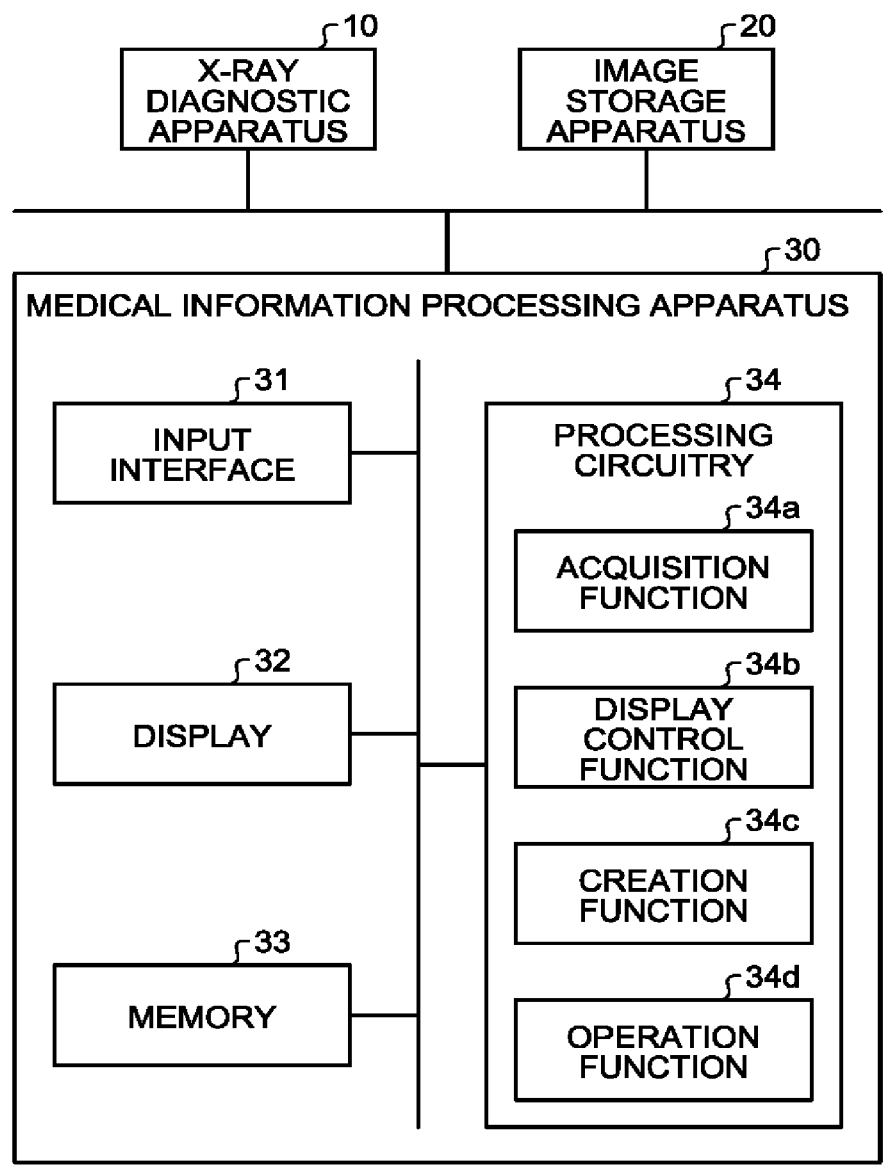
FIG. 1 is a block diagram illustrating a configuration example of an X-ray diagnostic system according to a first embodiment.

As illustrated in FIG. 1, an X-ray diagnostic system 1 according to the first embodiment includes an X-ray diagnostic apparatus 10, an image storage apparatus 20, and a medical information processing apparatus 30. FIG. 1 is a block diagram illustrating a configuration example of the X-ray diagnostic system 1 according to the first embodiment. As illustrated in FIG. 1, the X-ray diagnostic apparatus 10, the image storage apparatus 20, and the medical information processing apparatus 30 are connected to each other via a network.

The X-ray diagnostic apparatus 10 acquires X-ray image data from a subject P. For example, the X-ray diagnostic apparatus 10 performs rotational-imaging on a target region of the subject P to acquire a plurality of pieces of X-ray image data, and reconstructs three-dimensional X-ray image data (volume data) from the acquired pieces of X-ray image data. In this case, the three-dimensional X-ray image data is an example of three-dimensional medical image data. The X-ray diagnostic apparatus 10 transmits the reconstructed three-dimensional X-ray image data to the image storage apparatus 20 or the medical information processing apparatus 30.

The X-ray diagnostic apparatus 10 acquires direction and position of X-rays to be emitted that is set based on the three-dimensional medical image data, and emits X-rays in the acquired direction and the acquired position to acquire the pieces of X-ray image data. The X-ray diagnostic apparatus 10 displays the acquired pieces of X-ray image data in real time. For example, during surgery for the target region of the subject P, the X-ray diagnostic apparatus 10 displays the X-ray image data of the target region in real time. A configuration of the X-ray diagnostic apparatus 10 will be described later.

The image storage apparatus 20 stores the three-dimensional X-ray image data acquired by the X-ray diagnostic apparatus 10. For example, the image storage apparatus 20 is implemented by a computer device such as a server. In the present embodiment, the image storage apparatus 20 acquires the three-dimensional X-ray image data from the X-ray diagnostic apparatus 10 via the network, and causes a memory disposed inside or outside the apparatus to store the acquired three-dimensional X-ray image data.

The medical information processing apparatus 30 acquires the three-dimensional X-ray image data via the network, and performs various kinds of processing using the acquired three-dimensional X-ray image data. For example, the medical information processing apparatus 30 displays the acquired three-dimensional X-ray image data. By way of example, the medical information processing apparatus 30 performs rendering processing on the three-dimensional X-ray image data to generate a three-dimensional image for display, and displays the generated three-dimensional image. Examples of the rendering processing include volume rendering processing and maximum intensity projection (MIP). For example, the medical information processing apparatus 30 creates a figure indicating a movable region of a movable member of the X-ray diagnostic apparatus 10 based on the direction of the three-dimensional X-ray image data to be displayed, and displays the created figure indicating the movable region. Additionally, the medical information processing apparatus 30 receives setting of the direction of X-rays to be emitted from an operator who has referred to the three-dimensional X-ray image data and the figure indicating the movable region, and transmits the received setting of direction to the X-ray diagnostic apparatus 10. For example, the medical information processing apparatus 30 is implemented by a computer device such as a workstation.

As illustrated in FIG. 1, the medical information processing apparatus 30 includes an input interface 31, a display 32, a memory 33, and processing circuitry 34.

The input interface 31 is implemented by a trackball, a switch, a button, a mouse, and a keyboard for making various instructions, various settings, and the like, a touch pad for performing input operation by touching an operation surface, a touch screen obtained by integrating a display screen and a touch pad, a noncontact input circuit using an optical sensor, a voice input circuit, and the like. The input interface 31 converts an input operation received from the operator into an electric signal, and outputs the electric signal to the processing circuitry 34. The input interface 31 is not limited to an interface including a physical operation component such as a mouse and a keyboard. For example, examples of the input interface 31 include processing circuitry for an electric signal that receives the electric signal corresponding to the input operation from an external input appliance that is disposed separately from the medical information processing apparatus 30, and outputs the electric signal to the processing circuitry 34.

The display 32 displays various pieces of information. For example, the display 32 displays a graphical user interface (GUI) for receiving an instruction from the operator, and the three-dimensional X-ray image data. For example, the display 32 also displays the figure indicating the movable region of the movable member of the X-ray diagnostic apparatus 10. For example, the display 32 is a liquid crystal display or a cathode ray tube (CRT) display.

The medical information processing apparatus 30 may include a plurality of displays 32. For example, the medical information processing apparatus 30 may include, as the display 32, two displays (dual display) that are physically separated from each other. These displays 32 may be controlled to be associated with each other. For example, the displays 32 are controlled to display one continuous region. In this case, a display region of the display 32 is expanded corresponding to the number of the displays 32.

The memory 33 is, for example, implemented by a semiconductor memory element such as a random access memory (RAM) and a flash memory, a hard disk, an optical disc, and the like. For example, the memory 33 stores the three-dimensional X-ray image data acquired from the image storage apparatus 20. For example, the memory 33 stores a computer program for implementing a function of each circuit included in the medical information processing apparatus 30.

The processing circuitry 34 executes an acquisition function 34a, a display control function 34b, a creation function 34c, and an operation function 34d to control the entire operation of the medical information processing apparatus 30.

For example, the processing circuitry 34 reads out and executes a computer program corresponding to the acquisition function 34a from the memory 33 to acquire the three-dimensional X-ray image data from the X-ray diagnostic apparatus 10 or the image storage apparatus 20, and causes the memory 33 to store the three-dimensional X-ray image data. For example, the processing circuitry 34 reads out and executes a computer program corresponding to the display control function 34b from the memory 33 to cause the display 32 to display the three-dimensional X-ray image data. For example, the processing circuitry 34 reads out and executes a computer program corresponding to the creation function 34c from the memory 33 to create the figure indicating the movable region of the movable member of the X-ray diagnostic apparatus 10 based on the direction of the three-dimensional X-ray image data on the display 32. For example, the processing circuitry 34 reads out and executes a computer program corresponding to the display control function 34b from the memory 33 to cause the display 32 to further display the figure indicating the movable region of the movable member of the X-ray diagnostic apparatus 10.

In the medical information processing apparatus 30 illustrated in FIG. 1, each of processing functions is stored in the memory 33 as a computer-executable program. The processing circuitry 34 is a processor that reads out and executes a computer program from the memory 33 to implement a function corresponding to each computer program. In other words, the processing circuitry 34 that has read out each computer program has a function corresponding to the read-out computer program. In the description about FIG. 1, the acquisition function 34a, the display control function 34b, the creation function 34c, and the operation function 34d are assumed to be implemented by the single processing circuitry 34. However, a plurality of independent processors may be combined to constitute the processing circuitry 34, and each of the processors may execute a computer program to implement a function.

Figure 2:
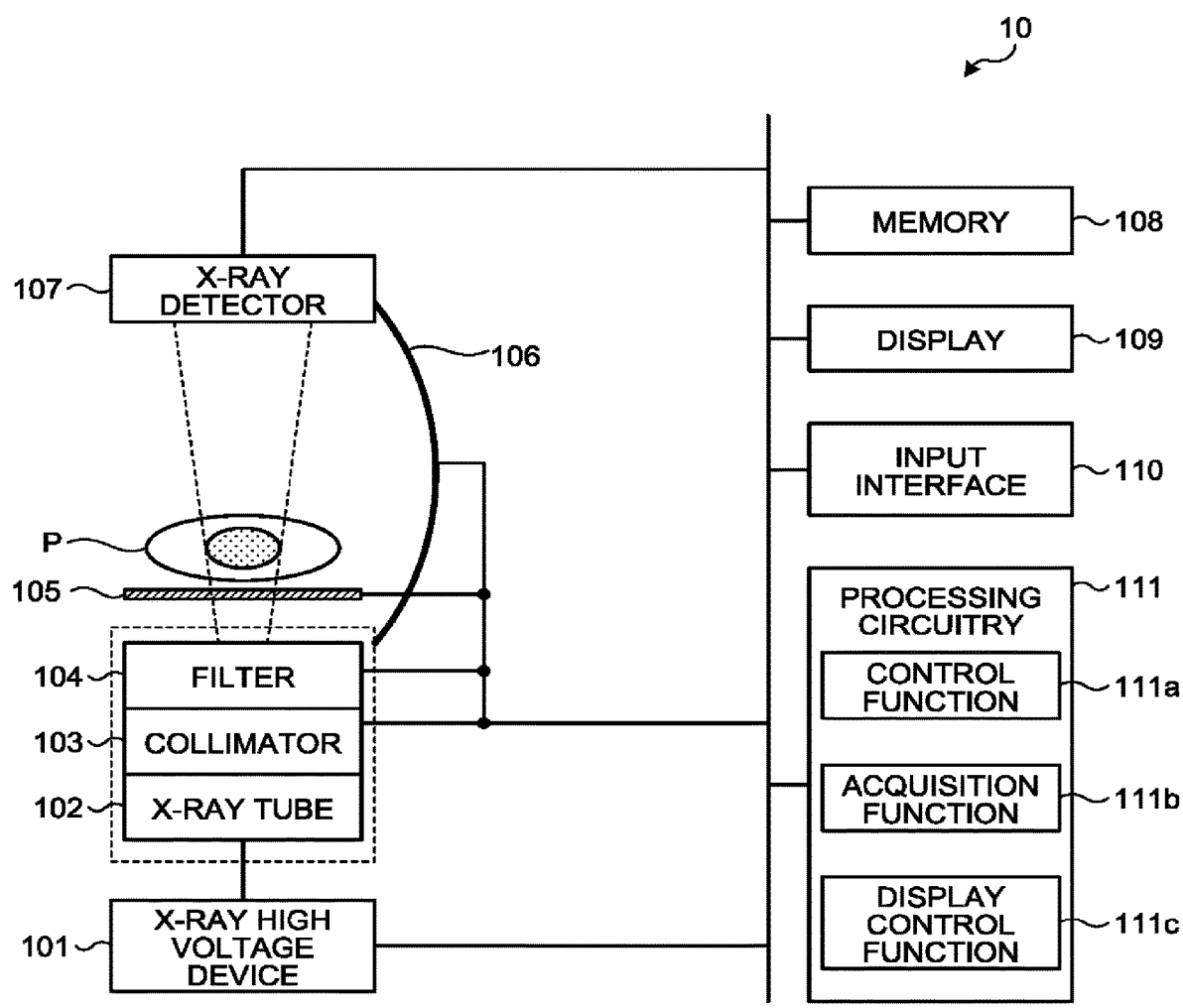
FIG. 2 is a block diagram illustrating a configuration example of an X-ray diagnostic apparatus according to the first embodiment.

Next, the following describes the X-ray diagnostic apparatus 10 that acquires the X-ray image data with reference to FIG. 2. FIG. 2 is a block diagram illustrating a configuration example of the X-ray diagnostic apparatus 10 according to the first embodiment. As illustrated in FIG. 2, the X-ray diagnostic apparatus 10 includes an X-ray high voltage device 101, an X-ray tube 102, a collimator 103, a filter 104, a tabletop 105, a C-arm 106, an X-ray detector 107, a memory 108, a display 109, an input interface 110, and processing circuitry 111.

The X-ray high voltage device 101 supplies high voltage to the X-ray tube 102 under control by the processing circuitry 111. For example, the X-ray high voltage device 101 includes a high voltage generation device that includes electric circuitry such as a transformer and a rectifier and generates high voltage to be applied to the X-ray tube 102, and an X-ray control device that controls output voltage corresponding to X-rays emitted from the X-ray tube 102. The high voltage generation device may be a transformer system or an inverter system.

The X-ray tube 102 is a vacuum tube including a cathode (filament) that generates a thermoelectron and an anode (target) that generates X-rays when the thermoelectron collides therewith. The X-ray tube 102 emits the thermoelectron to the anode from the cathode by using the high voltage supplied from the X-ray high voltage device 101 to generate X-rays.

The collimator (also referred to as an X-ray collimation device) 103 includes, for example, four slidable diaphragm blades. By sliding the diaphragm blades, the collimator 103 collimates X-rays generated by the X-ray tube 102 to be emitted to the subject P. In this case, the diaphragm blade is a plate member constituted of lead and the like, and disposed near an X-ray irradiation port of the X-ray tube 102 for adjusting an irradiation range of X-rays. For example, the collimator 103 includes a driving mechanism such as a motor and an actuator, and controls the irradiation range of X-rays under control by the processing circuitry 111 (described later). For example, the collimator 103 applies driving voltage to the driving mechanism in accordance with a control signal received from the processing circuitry 111 to adjust an opening of the diaphragm blades, and controls the irradiation range of X-rays emitted to the subject P.

To reduce an exposure dose for the subject P and improve image quality of the X-ray image data, the filter 104 changes radiation quality of X-rays transmitted therethrough depending on material or a thickness thereof. The filter 104 reduces soft ray components that are easily absorbed by the subject P, or reduces high energy components that cause contrast of the X-ray image data to be lowered. The filter 104 changes the dose and the irradiation range of X-rays depending on material, a thickness, a position, and the like thereof, and attenuates X-rays so that distribution of X-rays emitted from the X-ray tube 102 to the subject P becomes predetermined distribution. For example, the filter 104 includes a driving mechanism such as a motor and an actuator, and moves by operating the driving mechanism under control by the processing circuitry 111 (described later). For example, the filter 104 applies driving voltage to the driving mechanism in accordance with a control signal received from the processing circuitry 111 to adjust the position of the filter 104, and controls dose distribution of X-rays emitted to the subject P.

The tabletop 105 is a bed on which the subject P is placed, and arranged on a couch (not illustrated). The subject P is not included in the X-ray diagnostic apparatus 10. For example, the couch includes a driving mechanism such as a motor and an actuator, and controls movement/inclination of the tabletop 105 by operating the driving mechanism under control by the processing circuitry 111 (described later). For example, the couch applies driving voltage to the driving mechanism in accordance with a control signal received from the processing circuitry 111 to move or incline the tabletop 105.

The C-arm 106 holds the X-ray tube 102, the collimator 103, and the filter 104, and holds the X-ray detector 107 to be opposed thereto across the subject P. For example, the C-arm 106 includes a driving mechanism such as a motor and an actuator, and rotates or moves by operating the driving mechanism under control by the processing circuitry 111 (described later). For example, the C-arm 106 applies driving voltage to the driving mechanism in accordance with a control signal received from the processing circuitry 111 to rotate/move the X-ray tube 102, the collimator 103, the filter 104, and the X-ray detector 107 with respect to the subject P, and controls an irradiation position and an irradiation angle of X-rays. FIG. 2 exemplifies a case in which the X-ray diagnostic apparatus 10 is a single plane apparatus, but the embodiment is not limited thereto. The X-ray diagnostic apparatus 10 may be a biplane apparatus.

The X-ray detector 107 is, for example, an X-ray plane detector (flat panel detector: FPD) including detection elements arranged in a matrix. The X-ray detector 107 detects X-rays that are emitted from the X-ray tube 102 and transmitted through the subject P, and outputs, to the processing circuitry 111, a detection signal corresponding to a dose of the detected X-rays. The X-ray detector 107 may be a detector of indirect conversion type including a grid, a scintillator array, and an optical sensor array, or a detector of direct conversion type including a semiconductor element that converts incoming X-rays into an electric signal.

The memory 108 is, for example, implemented by a semiconductor memory element such as a RAM and a flash memory, a hard disk, an optical disc, and the like. For example, the memory 108 receives and stores the X-ray image data acquired by the processing circuitry 111. The memory 108 also stores computer programs corresponding to various functions that are read out and executed by the processing circuitry 111.

The display 109 displays various pieces of information. For example, the display 109 displays a GUI for receiving an instruction from the operator, and various pieces of X-ray image data. For example, the display 109 is a liquid crystal display or a CRT display.

The input interface 110 is implemented by a trackball, a switch, a button, a mouse, and a keyboard for making various instructions, various settings, and the like, a touch pad for performing an input operation by touching an operation surface, a touch screen obtained by integrating a display screen and a touch pad, a noncontact input circuit using an optical sensor, a voice input circuit, and the like. The input interface 110 converts an input operation received from the operator into an electric signal, and outputs the electric signal to the processing circuitry 111. The input interface 110 is not limited to an interface including a physical operation component such as a mouse and a keyboard. For example, examples of the input interface 110 include processing circuitry for an electric signal that receives the electric signal corresponding to the input operation from an external input appliance that is disposed separately from the X-ray diagnostic apparatus 10, and outputs the electric signal to the processing circuitry 111.

The processing circuitry 111 executes a control function 111a, a acquisition function 111b, and a display control function 111c to control the entire operation of the X-ray diagnostic apparatus 10. For example, the processing circuitry 111 reads out and executes a computer program corresponding to the control function 111a from the memory 108 to control various functions of the processing circuitry 111 based on the input operation received from the operator via the input interface 110.

The processing circuitry 111 reads out and executes a computer program corresponding to the acquisition function 111b from the memory 108 to acquire the X-ray image data. For example, the acquisition function 111b controls the X-ray high voltage device 101 to adjust voltage supplied to the X-ray tube 102, and controls ON/OFF and a dose of X-rays emitted to the subject P. The acquisition function 111b also controls the collimator 103 to adjust the opening of the diaphragm blades, and controls the irradiation range of X-rays emitted to the subject P. The acquisition function 111b also controls the filter 104 to adjust the position of the filter 104, and controls the dose distribution of X-rays. The acquisition function 111b also controls the operation of the C-arm 106 to rotate or move the C-arm 106. For example, the acquisition function 111b also controls the operation of the couch to move or incline the tabletop 105. The acquisition function 111b also generates the X-ray image data based on the detection signal received from the X-ray detector 107, and stores the generated X-ray image data in the memory 108. In this case, the acquisition function 111b may perform various kinds of image processing on the X-ray image data stored in the memory 108. For example, the acquisition function 111b executes scattered ray correction and noise reduction processing using an image processing filter on the X-ray image data.

In a case of performing rotational-imaging, the acquisition function 111b emits X-rays to the subject P while rotating the C-arm 106, and acquires a plurality of pieces of X-ray image data at a predetermined frame rate. The acquisition function 111b reconstructs three-dimensional X-ray image data from the acquired pieces of X-ray image data. The acquisition function 111b transmits the reconstructed three-dimensional X-ray image data to the image storage apparatus 20 or the medical information processing apparatus 30.

The processing circuitry 111 reads out and executes a computer program corresponding to the display control function 111c from the memory 108 to display, on the display 109, the X-ray image data and the three-dimensional X-ray image data acquired by the acquisition function 111b. For example, the processing circuitry 111 generates a three-dimensional X-ray image such as a volume rendering image and a multi planar reconstruction (MPR) image from the three-dimensional X-ray image data to be displayed on the display 109. The display control function 111c displays a GUI for receiving an instruction from the operator on the display 109.

The acquisition function 111b acquires the direction of X-rays to be emitted that is set based on the three-dimensional X-ray image data, and emits X-rays in the acquired direction to acquire a plurality of pieces of X-ray image data. The display control function 111c displays the acquired pieces of X-ray image data in real time. For example, during surgery for the target region of the subject P, the display control function 111c displays the X-ray image data of the target region on the display 109 in real time.

In the X-ray diagnostic apparatus 10 illustrated in FIG. 2, each of the processing functions is stored in the memory 108 as a computer-executable program. The processing circuitry 111 is a processor that reads out and executes a computer program from the memory 108 to implement a function corresponding to each computer program. In other words, the processing circuitry 111 that has read out each computer program has a function corresponding to the read-out computer program. In the description about FIG. 2, the control function 111a, the acquisition function 111b, and the display control function 111c are assumed to be implemented by the single processing circuitry 111. However, a plurality of independent processors may be combined to constitute the processing circuitry 111, and each of the processors may execute a computer program to implement a function. The processing functions included in the processing circuitry 111 may be implemented by being appropriately distributed or integrated in a single processing circuit or a plurality of processing circuits.

The word of "processor" used in the above description means, for example, a circuit such as a central processing unit (CPU), a graphics processing unit (GPU), an application specific integrated circuit (ASIC), or a programmable logic device (for example, a simple programmable logic device (SPLD), a complex programmable logic device (CPLD), and a field programmable gate array (FPGA)). The processor reads out and executes a computer program stored in the memory 33 or the memory 108 to implement the function. Instead of storing the computer program in the memory 33 or the memory 108, the computer program may be configured to be directly incorporated in a circuit of the processor. In this case, the processor reads out and executes the computer program incorporated in the circuit to implement a function. The processor according to the present embodiment is not necessarily configured to be a single circuit for each processor. A plurality of independent circuits may be combined to constitute one processor to implement the function thereof.

The X-ray diagnostic system 1 including the medical information processing apparatus 30 has been described above. With such a configuration, the medical information processing apparatus 30 in the X-ray diagnostic system 1 facilitates the setting of the direction of X-rays to be emitted through processing performed by the processing circuitry 34 that is described below in detail. The following describes the processing performed by the medical information processing apparatus 30 according to the first embodiment in detail.

First, the acquisition function 111b of the X-ray diagnostic apparatus 10 acquires the three-dimensional X-ray image data. For example, the acquisition function 111b performs rotational-imaging on the target region of the subject P to acquire a plurality of pieces of X-ray image data, and reconstructs the three-dimensional X-ray image data from the acquired pieces of X-ray image data. Next, the acquisition function 111b transmits the reconstructed three-dimensional X-ray image data to the image storage apparatus 20. In this case, the image storage apparatus 20 stores the three-dimensional X-ray image data transmitted from the X-ray diagnostic apparatus 10 in a memory disposed inside or outside the device.

Next, the acquisition function 34a of the medical information processing apparatus 30 acquires the three-dimensional X-ray image data from the image storage apparatus 20. The acquisition function 34a may acquire the three-dimensional X-ray image data from the X-ray diagnostic apparatus 10 without using the image storage apparatus 20. The acquisition function 34a then causes the memory 33 to store the acquired three-dimensional X-ray image data.

Figure 3:
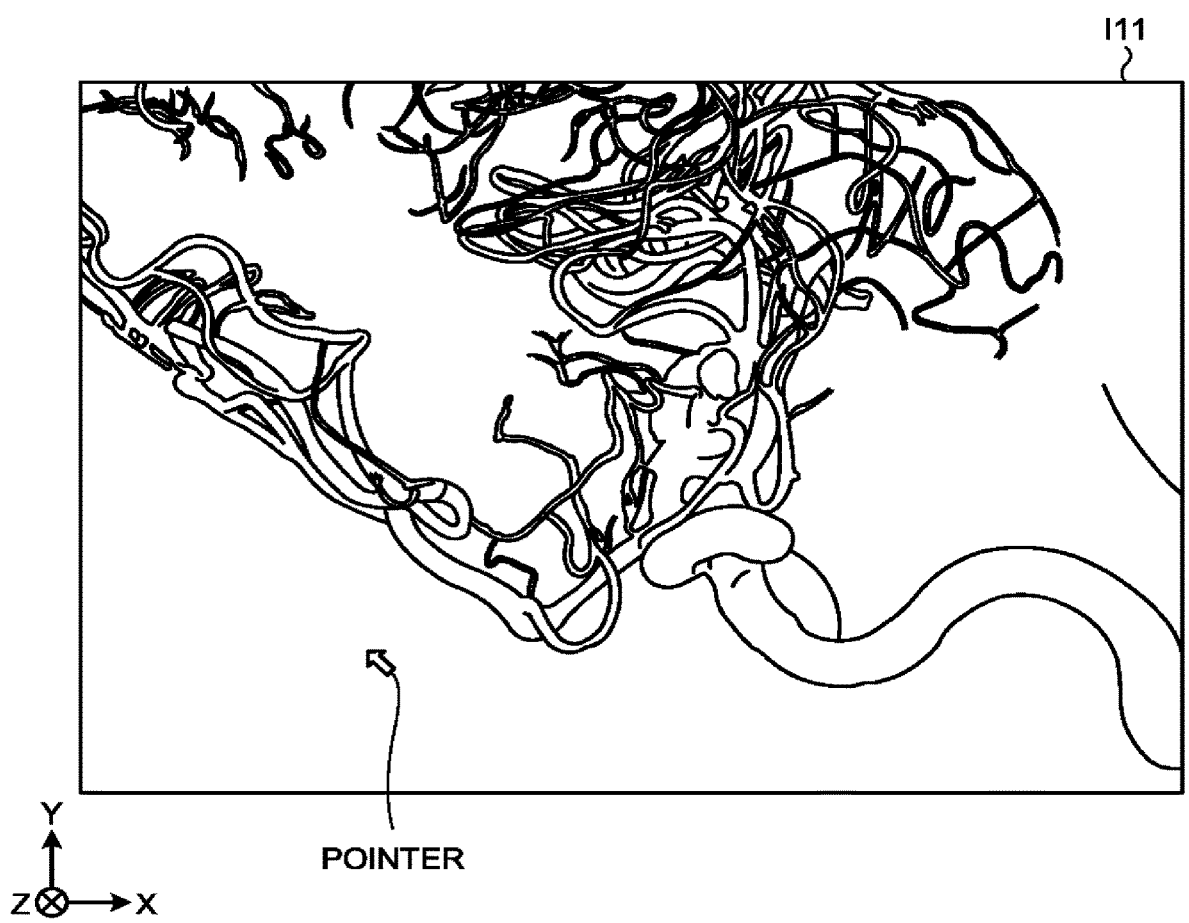
FIG. 3 is a diagram illustrating a display example of three-dimensional X-ray image data according to the first embodiment.

Next, the display control function 34b reads out the three-dimensional X-ray image data from the memory 33, and causes the display 32 to display the read-out three-dimensional X-ray image data. For example, as illustrated in FIG. 3, the processing circuitry 111 performs volume rendering processing on the three-dimensional X-ray image data to generate a three-dimensional X-ray image I11, and causes the display 32 to display the generated three-dimensional X-ray image I11. FIG. 3 is a diagram illustrating a display example of the three-dimensional X-ray image data according to the first embodiment.

FIG. 3 illustrates a pointer together with the three-dimensional X-ray image I11. The pointer is operated by the operator via the input interface 31 that is implemented by a mouse, a trackball, a joystick, a touch pad, and the like. For example, the operator can input an operation of rotating direction of the three-dimensional X-ray image I11 on the display 32 by using the pointer.

By way of example, the operator performs a drag operation using a mouse to move a position of the pointer on the three-dimensional X-ray image I11, and inputs the operation of rotating the direction of the three-dimensional X-ray image I11. At this point, the operation function 34d receives the operation input by the operator. The display control function 34b rotates the three-dimensional X-ray image I11 to be displayed in accordance with the operation received by the operation function 34d. For example, the display control function 34b rotates the three-dimensional X-ray image I11 to be displayed in accordance with a movement amount and a movement direction of the pointer using a center of the displayed three-dimensional X-ray image I11 as a rotation center. That is, the operation function 34d receives the operation of rotating the direction of the three-dimensional X-ray image I11 on the display 32 based on a displacement of the pointer displayed on the display 32.

Next, the creation function 34c creates a figure indicating the movable region of the movable member of the X-ray diagnostic apparatus 10 based on the direction of the three-dimensional X-ray image I11 on the display 32. For example, the creation function 34c creates the figure indicating the movable region triggered by the drag operation started by the operator who operates the mouse (when a button of the mouse is pushed). The following describes creation of the figure indicating the movable region performed by the creation function 34c.

First, the creation function 34c acquires the direction and the position of the three-dimensional X-ray image I11 on the display 32. In this case, the direction and the position of the three-dimensional X-ray image I11 on the display 32 means information about a position and a direction of the displayed three-dimensional X-ray image I11. For example, the creation function 34c acquires, as the direction and the position of the three-dimensional X-ray image I11 on the display 32, center coordinates of the displayed three-dimensional X-ray image I11 and a depth direction of the displayed three-dimensional X-ray image I11.

For example, the creation function 34c acquires, as the direction and the position of the three-dimensional X-ray image I11 on the display 32, the center coordinates of the displayed three-dimensional X-ray image I11 and the depth direction of the displayed three-dimensional X-ray image I11 in a coordinate system based on the subject P. In other words, the creation function 34c acquires, as the direction and the position of the three-dimensional X-ray image I11 on the display 32, information indicating which position on the subject P is viewed from which direction in the displayed three-dimensional X-ray image I11. By way of example, the creation function 34c acquires the center coordinates and the depth direction of the three-dimensional X-ray image I11 in the coordinate system based on the subject P by associating the three-dimensional X-ray image data with the position of the subject P based on a positional relation of the subject P with respect to the tabletop 105 and a positional relation of the X-ray tube 102 and the X-ray detector 107 with respect to the tabletop 105 in rotational-imaging of acquiring the three-dimensional X-ray image data related to the three-dimensional X-ray image I11. The following describes, as a Z-direction, the depth direction of the three-dimensional X-ray image I11 that is displayed at the time when the drag operation is started. Two directions that are orthogonal to the Z-direction and orthogonal to each other are described as an X-direction and a Y-direction.

The creation function 34c acquires information about the movable member of the X-ray diagnostic apparatus 10. In this case, among configurations of the X-ray diagnostic apparatus 10, the movable member of the X-ray diagnostic apparatus 10 means a configuration that can move or rotate to control the direction and the position of X-rays to be emitted to the subject P. For example, the movable member of the X-ray diagnostic apparatus 10 includes the X-ray tube 102, the collimator 103, the filter 104, the tabletop 105, the C-arm 106, and the X-ray detector 107 illustrated in FIG. 2.

For example, among movable members, the X-ray tube 102, the collimator 103, the filter 104, the C-arm 106, and the X-ray detector 107 rotate/move following rotation/movement of the C-arm 106 under control by the acquisition function 111b. Due to this, the movable members change the positional relation of the X-ray tube 102 and the X-ray detector 107 with respect to the subject P, and control a position irradiated with X-rays on the subject P and the irradiation angle of X-rays with respect to the subject P. For example, the subject P is placed on the tabletop 105 among the movable members, and the tabletop 105 inclines or moves under control by the acquisition function 111b. Due to this, the movable member changes the positional relation of the X-ray tube 102 and the X-ray detector 107 with respect to the subject P, and controls the position irradiated with X-rays on the subject P and the irradiation angle of X-rays with respect to the subject P.

The information about the movable member means, for example, structural limitations on a rotation angle and a moving range that are caused when the movable member rotates/moves. For example, the creation function 34c acquires, as the information about the movable member, an angular range in which the C-arm 106 can rotate and a range in which the C-arm 106 can move. For example, the creation function 34c acquires, as the information about the movable member, an angular range in which the tabletop 105 can incline or a range in which the tabletop 105 can move. By way of example, the creation function 34c acquires information about the movable member from accessory information of the three-dimensional X-ray image data. By way of another example, the creation function 34c refers to the setting information of the X-ray diagnostic apparatus 10 via the network to acquire the information about the movable member.

Figure 4:
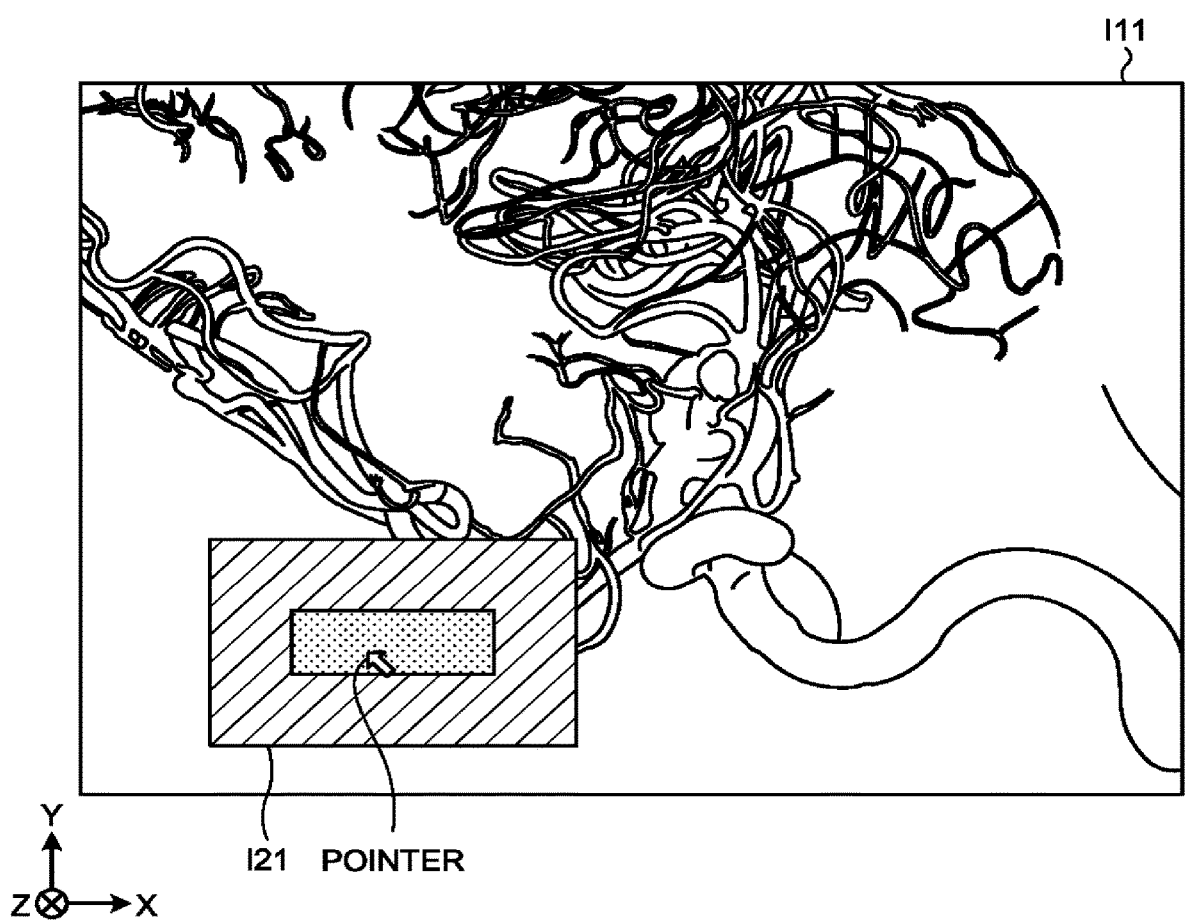
FIG. 4 is a diagram illustrating an example of a figure indicating a movable region of a movable member according to the first embodiment.

The creation function 34c then creates a figure indicating the movable region of the movable member based on the information about the movable member and the direction and the position of the three-dimensional X-ray image I11 on the display 32. For example, the creation function 34c creates a figure I21 illustrated in FIG. 4 as the figure indicating the movable region of the movable member. In this case, the creation function 34c creates the figure I21 so that the position of the pointer corresponds to the position indicated by the figure I21. FIG. 4 is a diagram illustrating an example of the figure I21 indicating the movable region of the movable member according to the first embodiment.

For example, the creation function 34c creates the figure I21 so that the direction of the three-dimensional X-ray image I11 that is rotated in accordance with the position of the pointer corresponds to the direction of X-rays to be emitted corresponding to the position indicated by the figure I21. For example, first, the creation function 34c acquires the direction of the three-dimensional X-ray image I11 associated with each position of the pointer. In this case, the direction of the three-dimensional X-ray image I11 rotates in accordance with movement of the pointer due to the operation function 34d, so that each position of the pointer is assumed to be associated with the direction of the three-dimensional X-ray image I11. Thus, the creation function 34c can acquire, from the operation function 34d, the direction of the three-dimensional X-ray image I11 associated with each position of the pointer. The creation function 34c then creates the figure I21 so that the direction of the three-dimensional X-ray image I11 substantially matches the direction of X-rays to be emitted for each position of the pointer.

Figure 5:
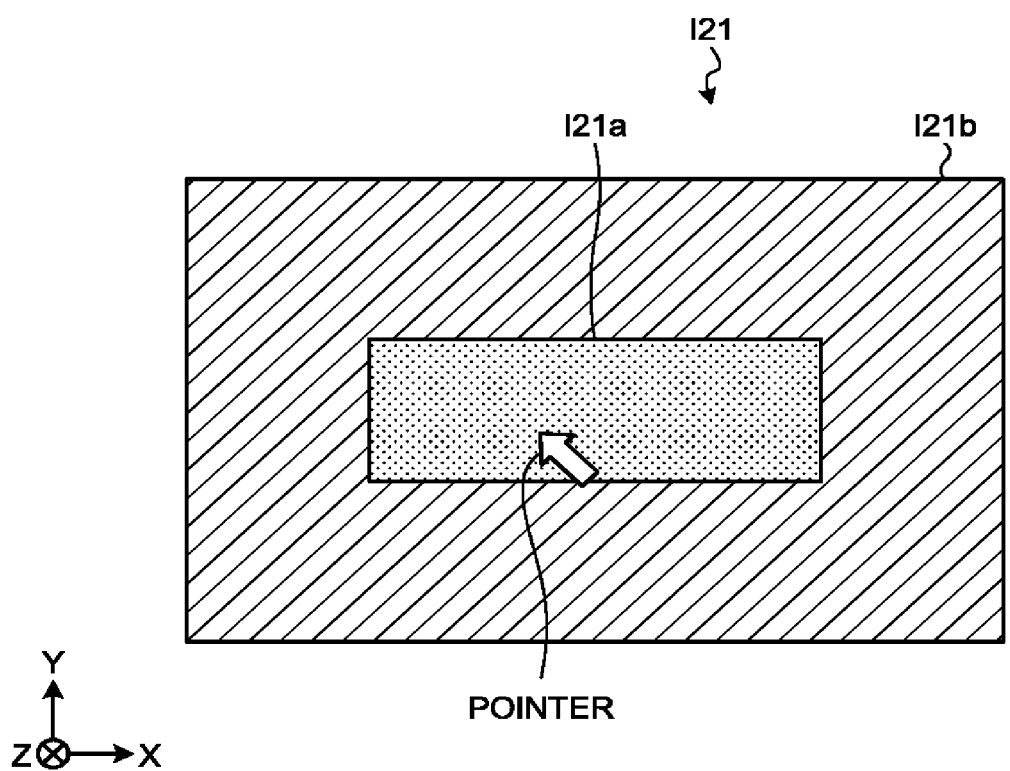
FIG. 5 is a diagram illustrating an example of a figure indicating the movable region of the movable member according to the first embodiment.

The following describes the figure I21 indicating the movable region in detail with reference to FIG. 5. FIG. 5 is a diagram illustrating an example of the figure I21 indicating the movable region of the movable member according to the first embodiment. As illustrated in FIG. 5, the figure I21 indicating the movable region is constituted of a movable region I21a and an immovable region I21b. FIG. 5 illustrates the movable region I21a with a dot pattern, and illustrates the immovable region I21b with a hatched pattern.

The movable region I21a indicates that the movable member can move to a position at which X-rays are emitted in parallel with the depth direction of the displayed three-dimensional X-ray image I11 with respect to the center coordinates of the three-dimensional X-ray image I11 that is displayed at the time when the pointer is positioned within the movable region I21a. That is, as the position of the pointer is moved by the operator, the direction of the three-dimensional X-ray image I11 displayed on the display 32 rotates, an angle with respect to the subject P in the depth direction of the three-dimensional X-ray image I11 is changed, and control performed by the movable member for emitting X-rays in parallel with the depth direction is also changed. In this case, the movable region I21a indicates that, so long as the pointer is positioned in the movable region I21a, X-rays can be emitted in parallel with the depth direction even if the depth direction of the three-dimensional X-ray image I11 is changed. In other words, the movable region I21a indicates that the target region can be displayed in real time in the same direction as the three-dimensional X-ray image I11 that is displayed in a case in which the pointer is positioned in the movable region I21a.

In contrast, the immovable region I21b indicates that the movable member cannot move to the position at which X-rays are emitted in parallel with the depth direction of the displayed three-dimensional X-ray image I11 with respect to the center coordinates of the three-dimensional X-ray image I11 that is displayed at the time when the pointer is positioned in the immovable region I21b. That is, the immovable region I21b indicates that X-rays cannot be emitted in parallel with the depth direction of the displayed three-dimensional X-ray image I11 in a case in which the pointer is positioned in the immovable region I21b. In other words, the immovable region I21b indicates that the target region cannot be displayed in real time in the same direction as the three-dimensional X-ray image I11 that is displayed in a case in which the pointer is positioned in the immovable region I21b.

For example, first, the creation function 34c determines which of the movable region I21a and the immovable region I21b corresponds to the position of the pointer illustrated in FIG. 5 (position at which the drag operation is started). Start of the drag operation is an example of an operation of designating a first position. That is, the creation function 34c determines whether the movable member can move to the position at which X-rays are emitted in parallel with the depth direction of the displayed three-dimensional X-ray image I11 with respect to the center coordinates of the displayed three-dimensional X-ray image I11. Specifically, based on the information about the movable member, the creation function 34c determines whether the X-ray tube 102 and the X-ray detector 107 can be arranged in parallel with the depth direction of the displayed three-dimensional X-ray image I11 across the center coordinates of the displayed three-dimensional X-ray image I11 in view of the structure of the movable member.

In this case, the creation function 34c may further use information about the arrangement of the X-ray diagnostic apparatus 10. In this case, first, the acquisition function 34a acquires information about the arrangement. For example, the acquisition function 34a acquires, as the information about the arrangement, information indicating whether the C-arm 106 is to be in the head-to-toe positioning or in the lateral positioning with respect to the tabletop 105 in acquiring the X-ray image data to be displayed in real time during surgery. The head-to-toe positioning means that the C-arm 106 is arranged in the longitudinal direction of the tabletop 105. The lateral positioning means that the C-arm 106 is arranged in the lateral direction of the tabletop 105. By way of example, the acquisition function 34a refers to the setting information of the X-ray diagnostic apparatus 10 via the network to acquire the information about the arrangement. The following describes a case in which the acquisition function 34a acquires information of setting the head-to-toe positioning as the information about the arrangement. In this case, the creation function 34c determines whether the X-ray tube 102 and the X-ray detector 107 can be arranged in parallel with the depth direction of the displayed three-dimensional X-ray image I11 across the center coordinates of the displayed three-dimensional X-ray image I11 in a case in which the C-arm 106 is positioned in the head-to-toe direction.

For example, as the information about the arrangement, the acquisition function 34a acquires shapes and dimensions of the configurations of the X-ray diagnostic apparatus 10 and posture information of the subject P placed on the tabletop 105. The creation function 34c further determines whether the configurations of the X-ray diagnostic apparatus 10 interfere with each other or a configuration of the X-ray diagnostic apparatus 10 interferes with the subject P based on the information about the arrangement. The creation function 34c then determines whether the X-ray tube 102 and the X-ray detector 107 can be arranged in parallel with the depth direction of the displayed three-dimensional X-ray image I11 across the center coordinates of the displayed three-dimensional X-ray image I11 without causing interference.

That is, even in a case in which the angle and the position of the C-arm 106 is included in the angular range in which the C-arm 106 can rotate and the range in which the C-arm 106 can move at the time when the X-ray tube 102 and the X-ray detector 107 are arranged in parallel with the depth direction across the center coordinates, the C-arm 106 and the tabletop 105 may interfere with each other when the C-arm 106 is arranged at the angle and at the position. In such a case, the creation function 34c determines that the X-ray tube 102 and the X-ray detector 107 cannot be arranged in parallel with the depth direction across the center coordinates.

Similarly, the creation function 34c determines which of the movable region I21a and the immovable region I21b corresponds to each position of the moved pointer. That is, the creation function 34c determines, in a case in which the pointer is moved from the position at which the drag operation is started and the direction of the three-dimensional X-ray image I11 rotates, whether the movable member can move to the position at which X-rays are emitted in parallel with the depth direction of the rotated three-dimensional X-ray image I11 with respect to the center coordinates of the rotated three-dimensional X-ray image I11, for each position around the position at which the drag operation is started. In this case, the operation of moving the pointer is an example of the operation of designating a displacement from the first position. Due to this, as illustrated in FIG. 5, the creation function 34c determines which of the movable region I21a and the immovable region I21b corresponds to each position around the position at which the drag operation is started, and creates the figure I21 indicating the movable region.

In this case, the creation function 34c may create the figure I21 to include at least one movable region I21a. For example, the creation function 34c successively determines which of the movable region I21a and the immovable region I21b corresponds to each position in a radial direction starting from the position at which the drag operation is started to a boundary between the movable region I21a and the immovable region I21b. Due to this, the creation function 34c extracts the boundary between the movable region I21a and the immovable region I21b, and extracts at least one movable region I21a. The creation function 34c causes a rectangular region surrounding the extracted movable region I21a and a region in a range of a predetermined distance from the extracted boundary to be the immovable region I21b to create the figure I21 indicating the movable region.

In the description about FIG. 5, the figure I21 indicating the movable region has a rectangular shape. However, the shape of the figure I21 indicating the movable region is optional. For example, the creation function 34c creates the figure I21 indicating the movable region to have a circular shape by determining which of the movable region I21a and the immovable region I21b corresponds to each position in a range of a predetermined distance from the position at which the drag operation is started. For convenience of explanation, FIG. 5 illustrates the movable region I21a as a rectangle, but the shape of the movable region I21a is not limited to the rectangle.

As illustrated in FIG. 4, the display control function 34b causes the display 32 to further display the figure I21 indicating the movable region created by the creation function 34c. In this case, the display control function 34b may cause the figure I21 indicating the movable region to be displayed in a non-transmissive manner as illustrated in FIG. 4, or in a transmissive manner. The display control function 34b may also cause the movable region I21a and the immovable region I21b to be displayed in different modes. For example, the display control function 34b may cause a figure in which the movable region I21a and the immovable region I21b are color-coded, or a figure in which transmittance is different between the movable region I21a and the immovable region I21b to be displayed as the figure I21 indicating the movable region.

The operator can input an operation of rotating the direction of the three-dimensional X-ray image I11 while referring to the figure I21 indicating the movable region. For example, first, the creation function 34c creates the figure I21 indicating the movable region triggered by the fact that the operator who operates the mouse pushes the button of the mouse, and the display control function 34b causes the created figure I21 indicating the movable region to be displayed. In this case, by performing the drag operation while pushing the button of the mouse, the operator can input the operation of rotating the direction of the three-dimensional X-ray image I11. The operation function 34d receives the operation of rotating the direction of the three-dimensional X-ray image I11, and the display control function 34b rotates the direction of the three-dimensional X-ray image I11 to be displayed in accordance with the operation received by the operation function 34d.

Figure 6A:
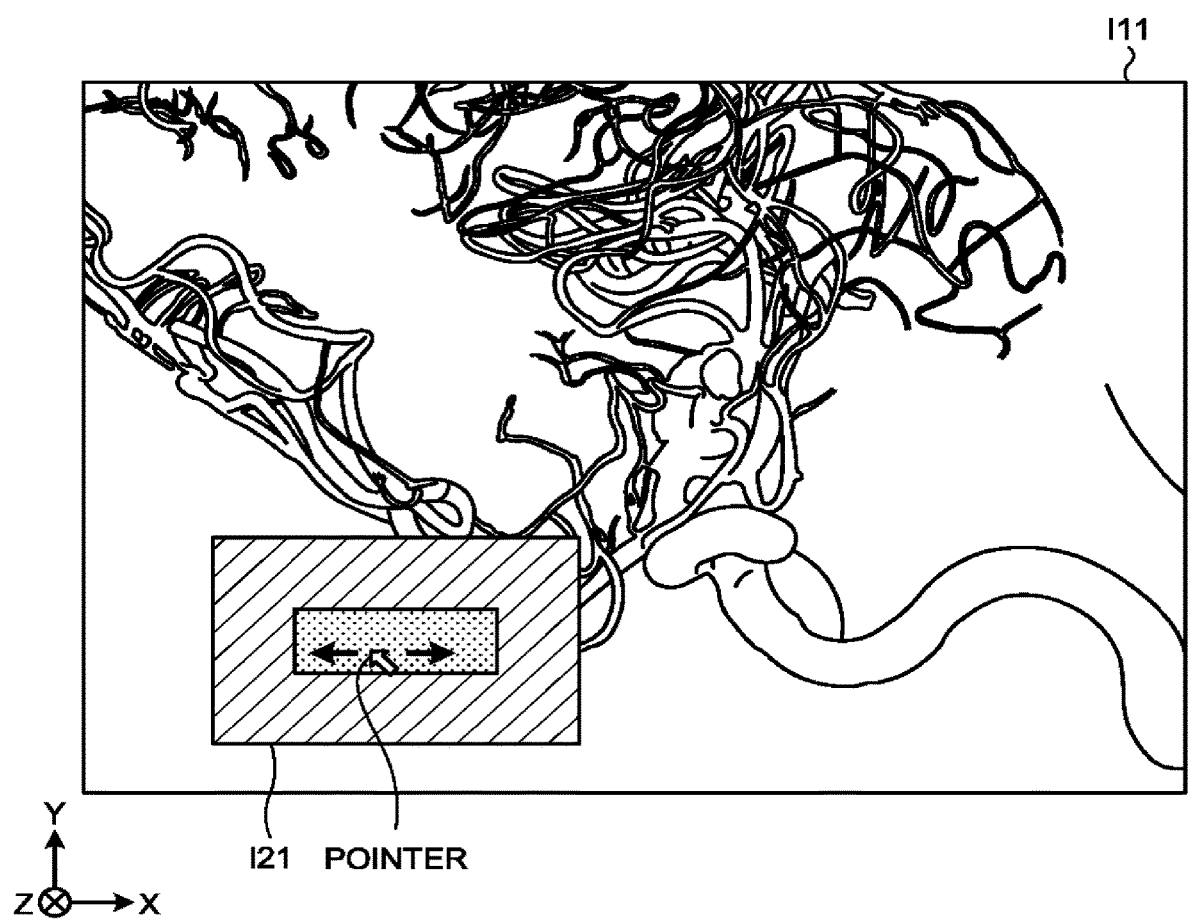
FIG. 6A is a diagram for explaining an example of an operation of rotating direction of the three-dimensional X-ray image data according to the first embodiment.

For example, in a case in which the operator performs the drag operation along a direction of an arrow illustrated in FIG. 6A, the operation function 34d receives the operation performed by the operator as an operation of rotating the direction of the three-dimensional X-ray image I11 about an axis parallel with the Y-direction as a rotation axis. The display control function 34b then rotates the direction of the three-dimensional X-ray image I11 to be displayed in accordance with the operation received by the operation function 34d. For example, the display control function 34b causes the three-dimensional X-ray image I11 to be displayed, the three-dimensional X-ray image I11 being rotated by an angle corresponding to the movement amount of the pointer about an axis passing through the center of the displayed three-dimensional X-ray image I11 in parallel with the Y-direction. FIG. 6A is a diagram for explaining an example of the operation of rotating the direction of the three-dimensional X-ray image data according to the first embodiment.

Figure 6B:
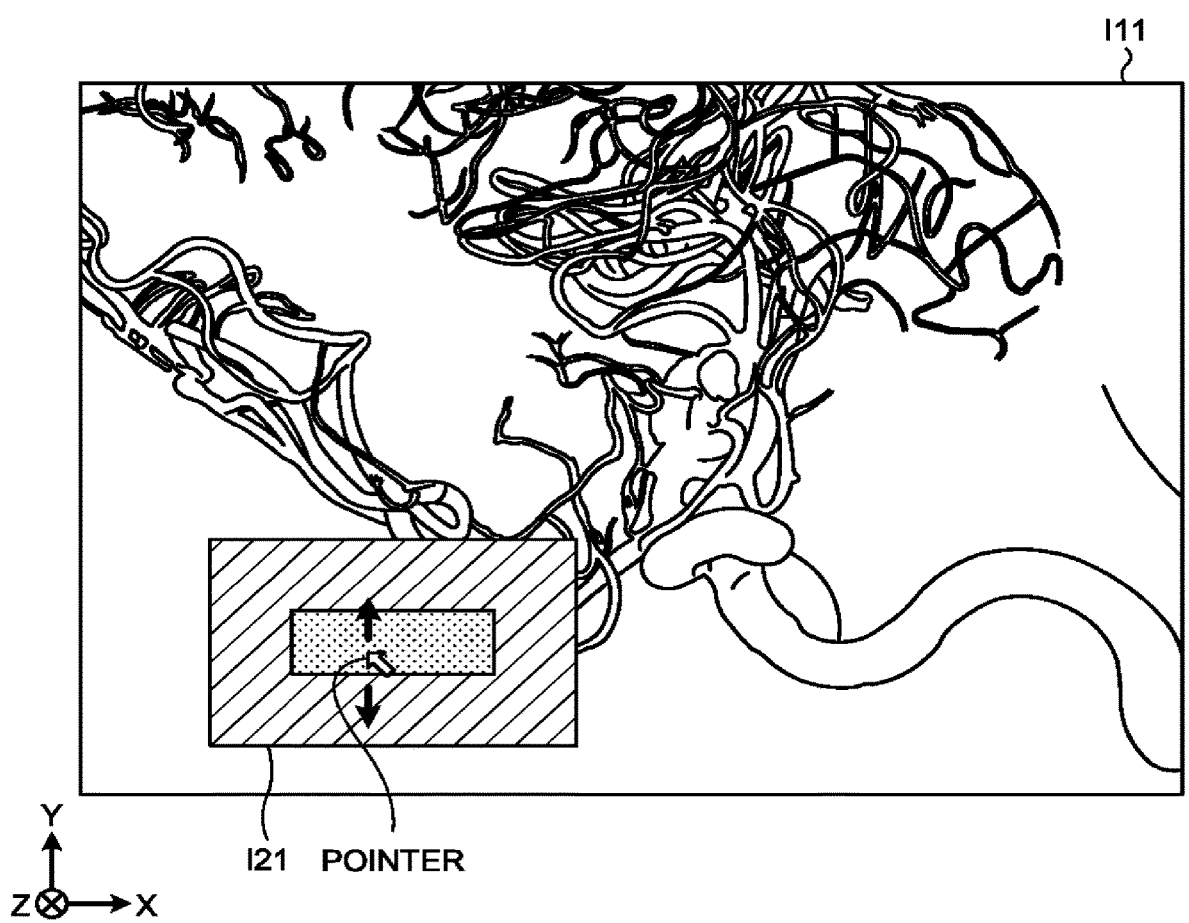
FIG. 6B is a diagram for explaining an example of the operation of rotating direction of the three-dimensional X-ray image data according to the first embodiment.

For example, in a case in which the operator performs the drag operation along a direction of an arrow illustrated in FIG. 6B, the operation function 34d receives the operation performed by the operator as an operation of rotating the direction of the three-dimensional X-ray image I11 about an axis parallel with the X-direction as a rotation axis. The display control function 34b then rotates the direction of the three-dimensional X-ray image I11 to be displayed in accordance with the operation received by the operation function 34d. For example, the display control function 34b causes the three-dimensional X-ray image I11 to be displayed, the three-dimensional X-ray image I11 being rotated by an angle corresponding to the movement amount of the pointer about an axis passing through the center of the displayed three-dimensional X-ray image I11 in parallel with the X-direction as the rotation axis. FIG. 6B is a diagram for explaining an example of the operation of rotating the direction of the three-dimensional X-ray image data according to the first embodiment.

The direction in which the drag operation is performed by the operator is not limited to a horizontal direction (the direction of the arrow illustrated in FIG. 6A) and a vertical direction (the direction of the arrow illustrated in FIG. 6B), and may be an oblique direction. In this case, for example, the operation function 34d receives the drag operation in the oblique direction as a combination of the drag operation in the horizontal direction and the drag operation in the vertical direction. The display control function 34b then rotates the direction of the three-dimensional X-ray image I11 to be displayed in accordance with the operation received by the operation function 34d. For example, the display control function 34b causes the three-dimensional X-ray image I11 to be displayed, the three-dimensional X-ray image I11 being rotated about the axis parallel with the X-direction as the rotation axis and further rotated about the axis parallel with the Y-direction as the rotation axis.

In this case, by combining rotation about the axis parallel with the X-direction as the rotation axis and rotation about the axis parallel with the Y-direction as the rotation axis, the display control function 34b can cause the three-dimensional X-ray image I11 rotated about an axis parallel with the Z-direction as the rotation axis to be displayed. That is, the display control function 34b can cause the direction of the three-dimensional X-ray image I11 to be rotated about an axis along any of the three directions, that is, the X-direction, the Y-direction, and the Z-direction.

While rotating the direction of the three-dimensional X-ray image I11 on the display 32, the operator selects the direction with which the target region can be easily observed. For example, the operator moves the pointer within the movable region I21a while referring to the figure I21 indicating the movable region, and ends the drag operation at the time when determining that the target region can be easily observed with the rotated direction of the three-dimensional X-ray image I11 to select the direction with which the target region can be easily observed. The position of the pointer at the time when the drag operation is ended is an example of a second position.

The operation function 34d receives, as the direction selected by the operator, the direction of the three-dimensional X-ray image I11 that is displayed at the time when the drag operation performed by the operator is ended, and transmits the received direction to the X-ray diagnostic apparatus 10. The X-ray diagnostic apparatus 10 sets the direction transmitted by the operation function 34d as the direction of X-rays to be emitted used for acquiring the X-ray image data. The display control function 34b may end display of the figure I21 indicating the movable region at the time when the drag operation performed by the operator is ended.

In a case in which the operator ends the drag operation in the immovable region I21b, the operation function 34d does not necessarily receive the selected direction. At this point, the display control function 34b may notify the operator that the selected direction cannot be set as the direction of X-rays to be emitted. In this case, the operator starts the drag operation again. The creation function 34c creates the figure indicating the movable region of the movable member again based on the direction of the three-dimensional X-ray image I11 on the display 32 triggered by the fact that the drag operation is started again. The display control function 34b causes the display 32 to further display the newly created figure indicating the movable region of the movable member. At this point, the operator selects the direction with which the target region can be easily observed while rotating the direction of the three-dimensional X-ray image I11 on the display 32. The operation function 34d then receives the selected direction, and transmits the received direction to the X-ray diagnostic apparatus 10. The X-ray diagnostic apparatus 10 sets the direction transmitted by the operation function 34d as the direction of X-rays to be emitted used for acquiring the X-ray image data.

In a case in which a display magnification of the three-dimensional X-ray image I11 is changed, the display control function 34b may cause the display 32 to display the figure I21 indicating the movable region in a size corresponding to the display magnification of the three-dimensional X-ray image I11. For example, first, the operation function 34d receives an operation of changing the display magnification from the operator. By way of example, the operation function 34d receives a wheel operation of the mouse performed by the operator as the operation of changing the display magnification of the three-dimensional X-ray image I11. In accordance with the operation received by the operation function 34d, the display control function 34b expands or reduces the three-dimensional X-ray image I11 to be displayed, and expands or reduces the figure I21 indicating the movable region to be displayed.

For example, in a case of receiving an operation of increasing the display magnification of the three-dimensional X-ray image I11 (zooming operation), the display control function 34b expands the figure I21 indicating the movable region to be displayed on the display 32. In other words, in a case of receiving the operation of increasing the display magnification of the three-dimensional X-ray image I11, when the operation of rotating the direction of the three-dimensional X-ray image I11 is performed, the display control function 34b reduces a rotation amount of the direction of the three-dimensional X-ray image I11 with respect to the movement amount of the pointer. Due to this, the display control function 34b can substantially fix change in a display region of the display 32 (moving speed of the display region) due to the movement amount of the pointer irrespective of the display magnification, and can cause the operator to select the direction more easily.

Thereafter, in surgery on the target region of the subject P, the X-ray diagnostic apparatus 10 displays the X-ray image data of the target region in real time based on the set direction of X-rays to be emitted. For example, first, the X-ray diagnostic apparatus 10 moves the movable member in accordance with the acquired direction. By way of example, in accordance with the center coordinates and the depth direction acquired as the direction, the X-ray diagnostic apparatus 10 moves the movable member so that the X-ray tube 102 and the X-ray detector 107 are arranged in parallel with the depth direction across the center coordinates. In this case, the direction acquired by the X-ray diagnostic apparatus 10 is set in the movable region I21a, so that the X-ray diagnostic apparatus 10 can move the movable member in accordance with the acquired direction.

The X-ray diagnostic apparatus 10 then emits X-rays to the subject P to acquire a plurality of pieces of X-ray image data, and displays the acquired pieces of X-ray image data in real time. At this point, the X-ray image data displayed in real time is displayed with the direction with which the target region can be easily observed that is selected by the operator while rotating the direction of the three-dimensional X-ray image I11 on the display 32.

In the description about FIG. 4, FIG. 5, FIG. 6A, and FIG. 6B, the immovable region is displayed in one mode different from that of the movable region. However, the embodiment is not limited thereto. That is, the medical information processing apparatus 30 may display the immovable region in a plurality of modes.

By way of example, the creation function 34c creates a figure I21c illustrated in FIG. 7 based on the information about the movable member, the information about the arrangement of the X-ray diagnostic apparatus 10, and the direction of the three-dimensional X-ray image I11 on the display 32. The display control function 34b causes the display 32 to display the figure I21c indicating the movable region. In this case, as illustrated in FIG. 7, the figure I21c includes a movable region I21d, an immovable region I21e, and an immovable region I21f. That is, the display control function 34b causes the immovable region to be displayed in a plurality of modes. FIG. 7 is a diagram illustrating an example of the figure indicating the movable region of the movable member according to the first embodiment.

Specifically, the movable region I21d indicates that the movable member can move to the position at which X-rays are emitted in parallel with the depth direction of the displayed three-dimensional X-ray image I11 with respect to the center coordinates of the three-dimensional X-ray image I11 that is displayed at the time when the pointer is positioned within the movable region I21d. That is, the movable region I21*d* indicates that, in a case of moving the pointer in the movable region I21*d* to rotate the three-dimensional X-ray image I11, the movable member can reach the position corresponding to the direction of the rotated three-dimensional X-ray image I11.

The immovable region I21*e* is an immovable region that is determined based on the information about the movable member. Specifically, the immovable region I21*e* indicates that, in view of the structure, the movable member cannot move to the position at which X-rays are emitted in parallel with the depth direction of the displayed three-dimensional X-ray image I11 with respect to the center coordinates of the three-dimensional X-ray image I11 that is displayed at the time when the pointer is positioned within the immovable region I21*e*. That is, the immovable region I21*e* indicates that, in a case of moving the pointer to the immovable region I21*e* to rotate the three-dimensional X-ray image I11, the movable member cannot reach the position corresponding to the direction of the rotated three-dimensional X-ray image I11.

The immovable region I21*f* is an immovable region that is determined based on the information about the arrangement of the X-ray diagnostic apparatus 10. Specifically, the immovable region I21*f* indicates that interference is caused when the movable member is moved to the position at which X-rays are emitted in parallel with the depth direction of the displayed three-dimensional X-ray image I11 with respect to the center coordinates of the three-dimensional X-ray image I11 that is displayed at the time when the pointer is positioned within the movable region I21*f*. That is, the immovable region I21*f* indicates that, in a case of moving the pointer to the immovable region I21*f* to rotate the three-dimensional X-ray image I11, the movable member cannot reach the position corresponding to the direction of the rotated three-dimensional X-ray image I11.

FIG. 2 exemplifies a case in which the X-ray diagnostic apparatus 10 is a single plane apparatus, but the embodiment is not limited thereto. The X-ray diagnostic apparatus 10 may be a biplane apparatus. In this case, the X-ray diagnostic apparatus 10 includes two arms that support the X-ray tube and the X-ray detector to be opposed to each other. For example, the X-ray diagnostic apparatus 10 includes a first arm that supports a first X-ray tube a first X-ray detector to be opposed to each other, and a second arm that supports a second X-ray tube and a second X-ray detector to be opposed to each other.

In a case in which the X-ray diagnostic apparatus 10 is a biplane apparatus, the creation function 34*c* further creates the figure indicating the movable region in consideration of interference between the first arm and the second arm. By way of example, the creation function 34*c* determines whether the second arm interferes with the first arm in a case of arranging the second arm on a lateral (L) side after the first arm is arranged on a frontal (F) side. The creation function 34*c* also determines whether the first arm interferes with the second arm in a case of arranging the first arm again after the second arm is arranged.

In the above description, the first arm is arranged firstly, but the second arm may be arranged firstly. In the above description, the first arm is arranged on the F side and the second arm is arranged on the L side, but the first arm may be arranged on the L side and the second arm may be arranged on the F side.

For example, the creation function 34*c* determines whether interference between the first arm and the second arm, interference between the first arm and the tabletop 105, interference between the second arm and the tabletop 105, and the like are caused as interference between the configurations of the X-ray diagnostic apparatus 10. For example, the creation function 34*c* determines whether interference between the first arm and the subject P, interference between the second arm and the subject P, or the like are caused as interference between a configuration of the X-ray diagnostic apparatus 10 and the subject P. The creation function 34*c* then creates the figure indicating the movable region based on a determination result of whether the interference between the configurations of the X-ray diagnostic apparatus 10 and the interference between a configuration of the X-ray diagnostic apparatus 10 and the subject P are caused.

In this case, the first arm and the second arm may operate in synchronization with each other. For example, the second arm may operate in synchronization with the first arm not to cause interference between the arms when the first arm operates under control by the acquisition function 111*b*. In a case in which the first arm and the second arm operate in synchronization with each other, the arm that operates synchronously may be brought into contact with a configuration other than the arm or the subject P while the interference between the arms is not caused.

For example, in a case in which the second arm operates in synchronization with the first arm in arranging the first arm, the second arm that operates synchronously may interfere with the tabletop 105 or the subject P while interference between the arms is not caused. Thus, the creation function 34*c* creates the figure indicating the movable region that is displayed in arranging the first arm by determining whether the second arm causes interference. More specifically, based on the information about the arrangement of the X-ray diagnostic apparatus 10, the creation function 34*c* determines whether the second arm that operates in synchronization with the first arm interfere with at least one of a configuration of the X-ray diagnostic apparatus 10 other than the first arm and the second arm, and the subject P when the first arm is operated, and creates the figure indicating the movable region that is displayed in arranging the first arm.

Next, the following describes an example of a processing procedure of the medical information processing apparatus 30 with reference to FIG. 8. FIG. 8 is a flowchart for explaining a series of procedures of processing performed by the medical information processing apparatus 30 according to the first embodiment. Step S101 is a step corresponding to the acquisition function 34*a*. Each of Step S102, Step S103, Step S106, and Step S108 is a step corresponding to the display control function 34*b*. Each of Step S104 and Step S105 is a step corresponding to the creation function 34*c*. Step S107 is a step corresponding to the operation function 34*d*.

First, the processing circuitry 34 acquires the three-dimensional X-ray image data from the X-ray diagnostic apparatus 10 or the image storage apparatus 20 (Step S101), and causes the memory 33 to store the acquired three-dimensional X-ray image data. Next, the processing circuitry 34 reads out the three-dimensional X-ray image data from the memory 33 to be displayed on the display 32 (Step S102). For example, the processing circuitry 34 creates a three-dimensional image for display by performing rendering processing on the three-dimensional X-ray image data, and causes the generated three-dimensional image to be displayed. At this point, the processing circuitry 34 determines whether to end the display of the three-dimensional X-ray image data (Step S103).

If the display is not ended (No at Step S103), the processing circuitry 34 determines whether the drag operation is started by the operator (Step S104). At this point, if the drag operation is not started (No at Step S104), the processing circuitry 34 returns the process to Step S103. On the other hand, if the drag operation is started by the operator (Yes at Step S104), the processing circuitry 34 creates the figure indicating the movable region of the movable member based on the direction of the three-dimensional X-ray image data on the display 32 (Step S105). The processing circuitry 34 causes the display 32 to further display the created figure indicating the movable region of the movable member (Step S106).

The processing circuitry 34 determines whether the operation of rotating the direction of the three-dimensional X-ray image data on the display 32 using the pointer displayed on the display 32 is received (Step S107). For example, the processing circuitry 34 determines whether the drag operation is received as the operation of rotating the direction. If the operation of rotating the direction is received (Yes at Step S107), the processing circuitry 34 rotates the direction of the three-dimensional X-ray image data on the display 32 in accordance with the received operation (Step S108). For example, by performing rendering processing on the three-dimensional X-ray image data in accordance with the received operation, the processing circuitry 34 generates the three-dimensional image the direction of which has been rotated, and causes the generated three-dimensional image to be displayed. Thereafter, the processing circuitry 34 returns the process to Step S107.

On the other hand, if the operation of rotating the direction is not received (No at Step S107), the processing circuitry 34 returns the process to Step S103. For example, in a case in which the drag operation performed by the operator is ended, the processing circuitry 34 assumes that the operation of rotating the direction is not received, and returns the process to Step S103. In this case, the processing circuitry 34 receives, as the direction selected by the operator, the direction of the three-dimensional X-ray image data that is displayed at the time when the drag operation is ended. If it is determined that the display is ended at Step S103 (Yes at Step S103), the processing circuitry 34 ends the process.

As described above, according to the first embodiment, the display control function 34b causes the display 32 to display the three-dimensional X-ray image data. The creation function 34c creates the figure indicating the movable region of the movable member based on the direction of the three-dimensional X-ray image data on the display 32. The display control function 34b causes the display 32 to further display the figure indicating the movable region. Accordingly, the medical information processing apparatus 30 according to the first embodiment can facilitate the setting of the direction of X-rays to be emitted. That is, the figure indicating the movable region is presented to the operator in setting the direction of X-rays to be emitted, so that the operator can easily set the direction of X-rays to be emitted while intuitively checking the movable region. With the medical information processing apparatus 30, the figure indicating the movable region is presented in setting the direction of X-rays to be emitted, so that it is possible to avoid a situation in which the direction that is selected by determining that the target region can be easily observed cannot be actually used, and reduce the time required for setting the direction of X-rays to be emitted.

Figure 9:
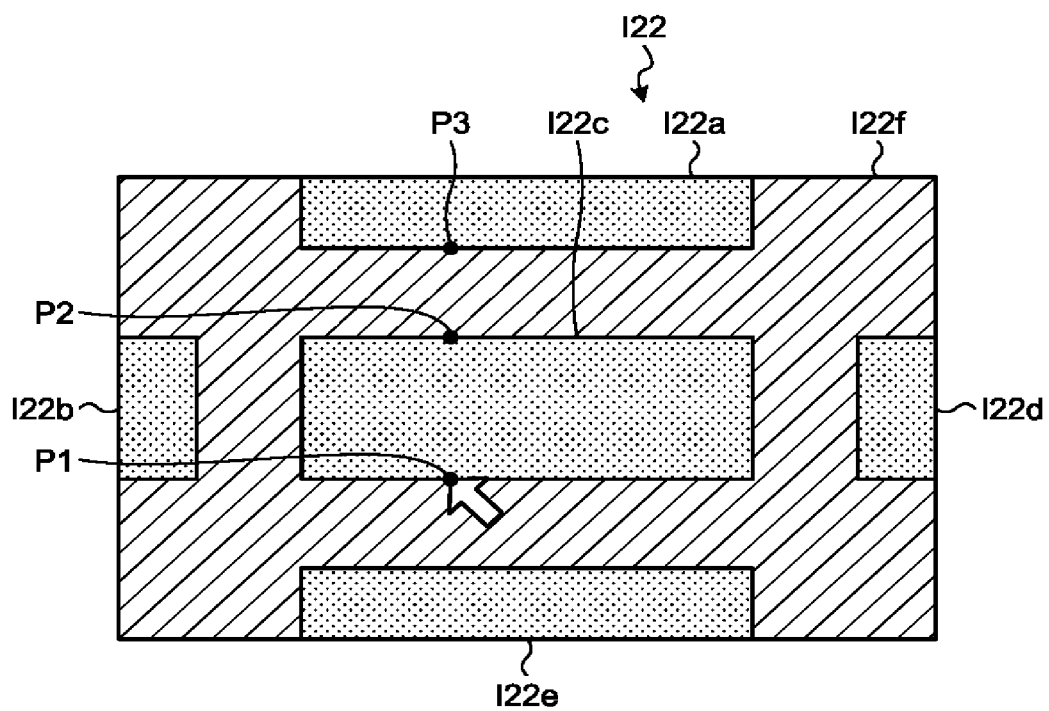
FIG. 9 is a diagram illustrating an example of a figure indicating the movable region of the movable member according to the first embodiment.

In the description about FIG. 5, described is the figure I21 indicating the movable region indicating one movable region (movable region I21a). However, the creation function 34c may create a figure indicating a plurality of movable regions. For example, the creation function 34c creates, as the figure indicating the movable regions, a figure I22 indicating the movable regions illustrated in FIG. 9. FIG. 9 is a diagram illustrating an example of the figure I22 indicating the movable region of the movable member according to the first embodiment.

As illustrated in FIG. 9, the figure I22 indicating the movable regions includes a movable region I22a, a movable region I22b, a movable region I22c, a movable region I22d, a movable region I22e, and an immovable region I22f. FIG. 9 illustrates the movable region I22a, the movable region I22b, the movable region I22c, the movable region I22d, and the movable region I22e with a dot pattern, and illustrates the immovable region I22f with a hatched pattern.

First, the creation function 34c creates the figure I22 indicating the movable regions based on the direction of the three-dimensional X-ray image I11 on the display 32. For example, first, the creation function 34c determines which of the movable region and the immovable region corresponds to the position of the pointer (position at which the drag operation is started) illustrated in FIG. 9. Additionally, the creation function 34c determines which of the movable region and the immovable region corresponds to each position of the moved pointer. Due to this, the creation function 34c determines which of the movable region and the immovable region corresponds to each position illustrated in the figure I22 indicating the movable regions, and creates the figure I22 indicating the movable regions. The display control function 34b causes the display 32 to display the figure I22 indicating the movable regions.

In this case, each position corresponding to the movable region I22a, the movable region I22b, the movable region I22c, the movable region I22d, and the movable region I22e corresponds to the identical direction of the three-dimensional X-ray image I11 on the display 32. For example, in a case in which the operator performs the drag operation to move the position of the pointer from a position P1 illustrated in FIG. 9 to a position P3 through a position P2, the display control function 34b rotates the direction of the three-dimensional X-ray image I11 by 360°. That is, the direction of the three-dimensional X-ray image I11 that is displayed at the time when the pointer is positioned at the position P1 is identical to the direction of the three-dimensional X-ray image I11 that is displayed at the time when the pointer is positioned at the position P3.

The operator rotates the direction of the three-dimensional X-ray image I11 on the display 32 while referring to the figure I22 indicating the movable regions, and ends the drag operation in the movable region to select the direction with which the target region can be easily observed. In this case, the operator may end the drag operation in any of the movable region I22a, the movable region I22b, the movable region I22c, the movable region I22d, and the movable region I22e. Thus, by displaying the figure I22 indicating the movable regions, the display control function 34b can cause the direction with which the target region can be easily observed to be selected more easily.

In the above description, the three-dimensional X-ray image data is exemplified as the three-dimensional medical image data, but the embodiment is not limited thereto. For example, in place of the three-dimensional X-ray image data, three-dimensional computed tomography (CT) image data or three-dimensional ultrasonic image data acquired for the target region of the subject P may be used.

For example, first, the acquisition function 34a acquires three-dimensional CT image data acquired for the target region of the subject P. For example, the acquisition function 34a acquires, via the network, the three-dimensional CT image data from an X-ray CT apparatus that has acquired the three-dimensional CT image data of the subject P. For example, the acquisition function 34a acquires the three-dimensional CT image data of the subject P from the image storage apparatus 20. The acquisition function 34a may acquire accessory information indicating a position and an angle of the three-dimensional CT image data with respect to the subject P together with the three-dimensional CT image data. Due to the accessory information, the position and the angle of the subject P placed on a tabletop included in the X-ray CT apparatus in acquiring the three-dimensional CT image data are associated with the position and the angle of the subject P placed on the tabletop 105.

Next, the display control function 34b causes the display 32 to display the three-dimensional CT image data. The creation function 34c creates the figure indicating the movable region of the movable member of the X-ray diagnostic apparatus 10 based on the direction of the three-dimensional CT image data on the display 32. The display control function 34b then causes the display 32 to further display the figure indicating the movable region of the movable member. Due to this, the operator can rotate the direction of the three-dimensional CT image data on the display 32 using the pointer displayed on the display 32 while referring to the figure indicating the movable region, and can more easily select the direction with which the target region can be easily observed.

The first embodiment describes a case of creating the figure indicating the movable region based on the direction of the three-dimensional medical image data on the display 32. In contrast, a second embodiment describes a case of creating the figure indicating the movable region based on the direction of the three-dimensional image data indicating the movable member of the X-ray diagnostic apparatus 10 on the display 32.

The medical information processing apparatus 30 according to the second embodiment has a configuration similar to that of the medical information processing apparatus 30 illustrated in FIG. 1, and is different from the medical information processing apparatus 30 illustrated in FIG. 1 in part of the processing performed by the acquisition function 34a, the display control function 34b, and the creation function 34c. Thus, a component having the same configuration as that described in the first embodiment is denoted by the same reference numeral as that in FIG. 1, and redundant description will not be repeated.

First, the acquisition function 34a acquires the three-dimensional image data indicating the movable member of the X-ray diagnostic apparatus 10. In this case, the three-dimensional image data indicating the movable member means, for example, model data indicating configurations included in movable members (the X-ray tube 102, the collimator 103, the filter 104, the tabletop 105, the C-arm 106, the X-ray detector 107, and the like) of the X-ray diagnostic apparatus 10. The three-dimensional image data indicating the movable members may indicate the entire X-ray diagnostic apparatus 10, or may indicate only part of the X-ray diagnostic apparatus 10 including the movable members.

The three-dimensional image data indicating the movable members may be model data corresponding to the shape, dimensions, and the like of each configuration included in the movable members of the X-ray diagnostic apparatus 10, or may be model data indicating a typical external appearance of each configuration. For example, the three-dimensional image data indicating the tabletop 105 among the movable members may be model data that is created in accordance with an actual shape and dimensions of the tabletop 105, or may be model data simply indicating a typical external appearance of the tabletop 105. For example, the acquisition function 34a acquires the three-dimensional image data indicating the movable members in advance via the network, or receives an input of the three-dimensional image data in advance via the input interface 31, and causes the memory 33 to store the three-dimensional image data.

For example, the three-dimensional image data indicating the movable members is used for selecting, before surgery for the subject P, the direction of X-rays to be emitted used for acquiring the X-ray image data to be displayed in real time during the surgery. By way of example, the operator selects the direction of X-rays to be emitted while rotating the direction of the three-dimensional image data indicating the movable members on the display 32 so that a standing position of the operator at the time of performing surgery for the subject P does not overlap with the movable members.

Figure 10:
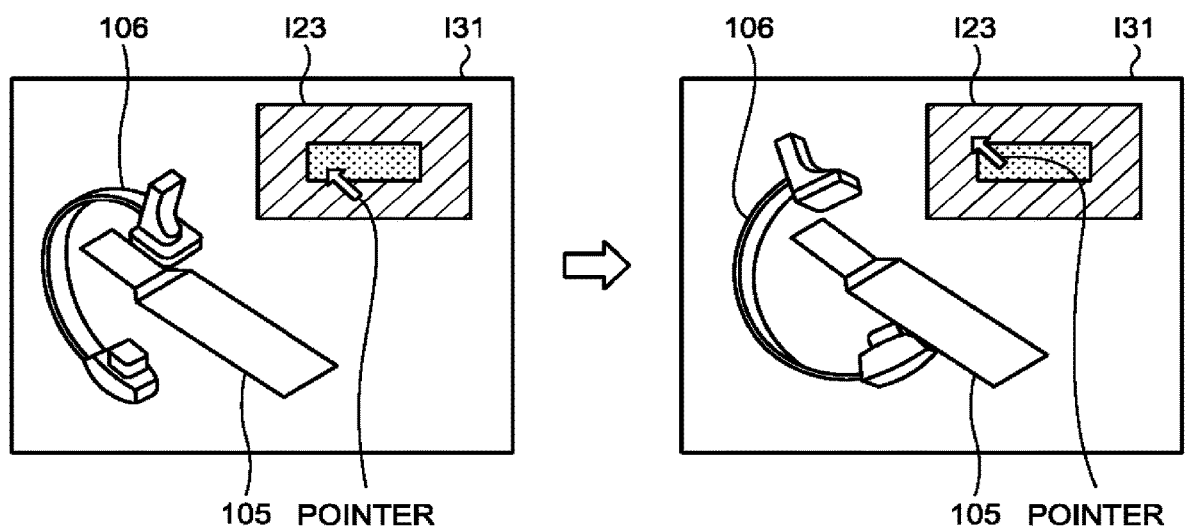
FIG. 10 is a diagram illustrating a display example of three-dimensional image data indicating movable members of an X-ray diagnostic apparatus according to a second embodiment.

The following describes three-dimensional image data I31 illustrated in FIG. 10 as an example of the three-dimensional image data indicating the movable members. FIG. 10 is a diagram illustrating a display example of the three-dimensional image data indicating the movable members of the X-ray diagnostic apparatus 10 according to the second embodiment. The three-dimensional image data I31 is model data indicating a positional relation between the C-arm 106 and the tabletop 105 in the X-ray diagnostic apparatus 10. In this case, the C-arm 106 supports the X-ray detector 107 and the X-ray tube 102, the collimator 103, and the filter 104 to be opposed to each other. The C-arm 106 rotates/moves under control by the acquisition function 111b to change the positional relation of the X-ray tube 102 and the X-ray detector 107 with respect to the subject P placed on the tabletop 105, and controls the position irradiated with X-rays on the subject P and the irradiation angle of X-rays with respect to the subject P. The tabletop 105 inclines/moves under control by the acquisition function 111b to change the positional relation of the subject P with respect to the X-ray tube 102 and the X-ray detector 107, and controls the position irradiated with X-rays on the subject P and the irradiation angle of X-rays with respect to the subject P.

First, as illustrated in the left figure of FIG. 10, the display control function 34b causes the display 32 to display the three-dimensional image data I31 and the pointer. For example, the operator can perform an operation of rotating the direction of the three-dimensional image data I31 on the display 32 using the pointer displayed on the display 32.

In this case, the direction and the position of the three-dimensional image data I31 on the display 32 means the direction and the position of X-rays to be emitted indicated by the displayed three-dimensional X-ray image I11. For example, the direction and the position of the three-dimensional image data I31 on the display 32 is coordinates of the position irradiated with X-rays on the subject P and the irradiation angle of X-rays with respect to the subject P in a case in which the subject P is placed on the tabletop 105 on the display 32. By way of example, the operator rotates the C-arm 106 on the display 32 or inclines the tabletop 105 on the display 32 using the pointer displayed on the display 32 to input the operation of rotating the direction of the three-dimensional image data I31 on the display 32.

Whether to rotate the C-arm 106 or incline the tabletop 105 for rotating the direction of the three-dimensional image data I31 on the display 32 may be selected in advance by the operator, or may be preset. The following describes a case in which the direction of the three-dimensional image data I31 on the display 32 rotates due to rotation of the C-arm 106 on the display 32.

After the three-dimensional image data I31 is displayed on the display 32 by the display control function 34b, the creation function 34c creates the figure indicating the movable region of the movable member of the X-ray diagnostic apparatus 10 based on the direction of the three-dimensional image data I31 on the display 32. For example, triggered by the drag operation started by the operator who operates the mouse (when the button of the mouse is pushed), the creation function 34c creates a figure I23 indicating the movable region as illustrated in the left figure of FIG. 10. FIG. 10 illustrates the movable region with a dot pattern, and illustrates the immovable region with a hatched pattern.

For example, first, the creation function 34c determines which of the movable region and the immovable region corresponds to the position of the pointer (position at which the drag operation is started) illustrated in the left figure of FIG. 10. Specifically, the creation function 34c determines whether the C-arm 106 can be arranged at the displayed position and angle in view of the structure of the movable members based on information about the movable members. In this case, the creation function 34c may further use information about the arrangement of the X-ray diagnostic apparatus 10. In determining whether interference is caused, the creation function 34c may take account of a configuration that is not displayed in the three-dimensional image data I31 (for example, a base supporting the C-arm 106, a supporting frame supporting the tabletop 105, and a base supporting the tabletop 105 and the supporting frame), and the subject P.

Similarly, the creation function 34c determines which of the movable region and the immovable region corresponds to each position of the moved pointer. That is, the creation function 34c determines, in a case in which the pointer is moved from the position at which the drag operation is started and the C-arm 106 rotates on the display 32, whether the C-arm 106 can be arranged at the position and the angle after the rotation for each position around the position at which the drag operation is started. Due to this, as illustrated in the left figure of FIG. 10, the creation function 34c determines which of the movable region and the immovable region corresponds to each position around the position at which the drag operation is started, and creates the figure I23 indicating the movable region. As illustrated in the left figure of FIG. 10, the display control function 34b causes the display 32 to further display the created figure I23 indicating the movable region.

In this case, the operator can input the operation of rotating the direction of the three-dimensional image data I31 on the display 32 while referring to the figure I23 indicating the movable region. For example, the operator rotates the C-arm 106 on the display 32 by performing the drag operation to rotate the direction of the three-dimensional image data I31 on the display 32. The operation function 34d receives the operation of rotating the direction of the three-dimensional image data I31, and the display control function 34b rotates the direction of the three-dimensional image data I31 to be displayed in accordance with the operation received by the operation function 34d.

For example, in a case in which the operator performs the drag operation from the position of the pointer illustrated in the left figure of FIG. 10 to the position of the pointer illustrated in the right figure of FIG. 10, the operation function 34d rotates the C-arm 106 on the display 32 to be displayed in accordance with a movement amount and a movement direction of the pointer. In a case illustrated in the right figure of FIG. 10, the display control function 34b may notify that the pointer is positioned in the immovable region. For example, in a case in which the pointer is positioned in the immovable region, the display control function 34b may display a message indicating that fact, or may change a color of part (the C-arm 106 and the like) of or the entire three-dimensional image data I31 to be displayed.

The operator then selects the direction of X-rays to be emitted used for acquiring the X-ray image data to be displayed in real time while rotating the direction of the three-dimensional image data I31 on the display 32. For example, the operator moves the pointer in the movable region while referring to the figure I23 indicating the movable region, and ends the drag operation at the time of determining that the standing position of the operator does not overlap with the C-arm 106 in performing surgery for the subject P to select the direction of X-rays to be emitted.

The operation function 34d receives, as the direction selected by the operator, the direction of the three-dimensional image data I31 that is displayed at the time when the drag operation performed by the operator is ended, and transmits the received direction to the X-ray diagnostic apparatus 10. The X-ray diagnostic apparatus 10 sets the direction transmitted by the operation function 34d as the direction of X-rays to be emitted used for acquiring the X-ray image data. The display control function 34b may end display of the figure I23 indicating the movable region at the time when the drag operation performed by the operator is ended.

Thereafter, in surgery for the target region of the subject P, the X-ray diagnostic apparatus 10 displays the X-ray image data of the target region in real time based on the set direction of X-rays to be emitted. For example, first, the X-ray diagnostic apparatus 10 moves the movable member in accordance with the acquired direction. By way of example, the X-ray diagnostic apparatus 10 acquires, as the direction and the position, the position irradiated with X-rays on the subject P that is placed on the tabletop 105 and the irradiation angle of X-rays with respect to the subject P, and moves the movable member so that the X-ray tube 102 and the X-ray detector 107 are arranged along the acquired irradiation angle across the acquired position. In this case, the direction acquired by the X-ray diagnostic apparatus 10 is set in the movable region, so that the X-ray diagnostic apparatus 10 can move the movable member in accordance with the acquired direction.

The X-ray diagnostic apparatus 10 then emits X-rays to the subject P to acquire a plurality of pieces of X-ray image data, and displays the acquired pieces of X-ray image data in real time. At this point, the C-arm 106 is arranged not to overlap with the standing position of the operator in performing surgery for the subject P, so that the C-arm 106 can be prevented from hindering the surgery by the X-ray diagnostic apparatus 10.

The first and the second embodiments have been described above. Alternatively, various different embodiments other than the first and the second embodiments may be employed.

In the embodiments described above, described is a case of creating the figure indicating the movable region of the movable member based on any one of the direction of the three-dimensional medical image data on the display 32 and the direction of the three-dimensional image data indicating the movable member on the display 32. However, the creation function 34c may create the figure indicating the movable region of the movable member based on both of the direction of the three-dimensional medical image data on the display 32 and the direction of the three-dimensional image data on the display 32.

For example, first, the display control function 34b associates the three-dimensional medical image data with the three-dimensional image data indicating the movable member to be displayed on the display 32. That is, the display control function 34b associates the three-dimensional medical image data with the three-dimensional image data to be displayed on the display 32 so that the center coordinates of the displayed three-dimensional medical image data are included in the irradiation position of X-rays indicated by the displayed three-dimensional image data, and the irradiation angle of X-rays indicated by the displayed three-dimensional image data matches the depth direction of the displayed three-dimensional medical image data. At this point, in a case in which the operation function 34d receives the drag operation and the like performed by the operator, the display control function 34b rotates the three-dimensional medical image data and the three-dimensional image data to be displayed while maintaining such a correspondence relation.

Next, the creation function 34c creates the figure indicating the movable region of the movable member based on the direction of the three-dimensional medical image data and the three-dimensional image data on the display 32. The display control function 34b causes the display 32 to further display the created figure indicating the movable region of the movable member. In this case, the display control function 34b may superimpose the figure indicating the movable region of the movable member on the three-dimensional medical image data to be displayed, may superimpose the figure indicating the movable region of the movable member on the three-dimensional image data to be displayed, or may cause the figure indicating the movable region of the movable member to be displayed at a position that is not superimposed on any of the three-dimensional medical image data and the three-dimensional image data. For example, the display control function 34b causes the figure indicating the movable region of the movable member at the position of the pointer at the time when the drag operation is started by the operator. Due to this, the operator can select the direction of X-rays to be emitted used for acquiring the X-ray image data to be displayed in real time so that the target region can be easily observed, and the standing position of the operator does not overlap with the movable member in performing surgery for the subject P.

In a case in which the medical information processing apparatus 30 includes a plurality of displays 32, the display control function 34b may cause the different displays 32 to display the figure indicating the movable region, the three-dimensional medical image data, and the three-dimensional image data. For example, in a case in which the medical information processing apparatus 30 includes two displays 32, the display control function 34b may cause a first display to display the three-dimensional medical image data, and may cause a second display to display the figure indicating the movable region of the movable member superimposed on the three-dimensional image data.

In the embodiments described above, the drag operation using the mouse is described as an example of the operation of rotating the direction of the three-dimensional medical image data or the three-dimensional image data on the display 32 using the pointer displayed on the display 32. However, the embodiment is not limited thereto. For example, the operation function 34d may receive two times of click operations in place of the drag operation. In this case, the operation function 34d receives the first click operation instead of the drag operation that is started, and receives the second click operation instead of the drag operation that is ended. The first click operation is an example of an operation of designating the first position. The second click operation is an example of an operation of designating a displacement from the first position. The position at which the second click operation is performed is an example of the second position. For example, the operation function 34d may receive an operation using a trackball, a joystick, a touch pad, and the like in place of the operation using the mouse.

The operation function 34d may receive an operation using a position designated by the operator on the display 32 in place of the operation using the pointer displayed on the display 32. That is, the operation function 34d may receive an operation of rotating the direction of the three-dimensional medical image data or the three-dimensional image data on the display 32 using the position designated by the operator on the display 32.

For example, in a case in which the input interface 31 and the display 32 are implemented by a touch screen, the operation function 34d receives a position on the touch screen touched by the operator as the position designated by the operator on the display 32. In this case, for example, triggered by the fact that the operator touches the touch screen, the creation function 34c creates the figure indicating the movable region so that the position designated on the touch screen corresponds to the position indicated by the figure indicating the movable region. For example, the creation function 34c creates the figure indicating the movable region so that the direction of the three-dimensional medical image data or the three-dimensional image data that is rotated in accordance with the position designated on the touch screen corresponds to the direction of X-rays to be emitted corresponding to the position indicated by the figure indicating the movable region.

The operation of touching the touch screen is an example of the operation of designating the first position. For example, in a case in which the operator slides the position on the touch screen touched by the operator, the display control function 34b rotates the direction of the three-dimensional medical image data or the three-dimensional image data to be displayed in accordance with the movement amount and the movement direction of the position on the touch screen touched by the operator. The operation of sliding a position to be touched on the touch screen is an example of the operation of designating a displacement from the first position. A position after sliding is an example of the second position.

In the embodiments described above, the X-ray tube 102, the collimator 103, the filter 104, the tabletop 105, the C-arm 106, and the X-ray detector 107 are described as the movable members among the configurations of the X-ray diagnostic apparatus 10, but the embodiment is not limited thereto. For example, the X-ray tube 102, the collimator 103, the filter 104, the C-arm 106, and the X-ray detector 107 may be set as the movable members assuming that the tabletop 105 is immovable. Alternatively, for example, only the tabletop 105 may be set as the movable member assuming that the X-ray tube 102, the collimator 103, the filter 104, the C-arm 106, and the X-ray detector 107 are immovable. For example, in a case in which the base supporting the C-arm 106 can be rotated or moved, the base may be included in the movable members. That is, the movable members may include all the configurations that can control the direction of X-rays to be emitted with respect to the subject P, or may include only selected part of the configurations used for controlling the direction of X-rays to be emitted among the configurations of the X-ray diagnostic apparatus 10.

The creation function 34c may create the figure indicating the movable region of the movable member in accordance with the configuration included in the movable member. For example, the creation function 34c creates, as the figure indicating the movable region, a figure indicating the movable region in a case in which the X-ray tube 102, the collimator 103, the filter 104, the tabletop 105, the C-arm 106, and the X-ray detector 107 are assumed to be the movable members, the movable region in a case in which the base supporting the C-arm 106 is also included in the movable members, and the immovable region. In this case, for example, the display control function 34b color-codes the three regions in different colors to be displayed on the display 32.

Figure 11:
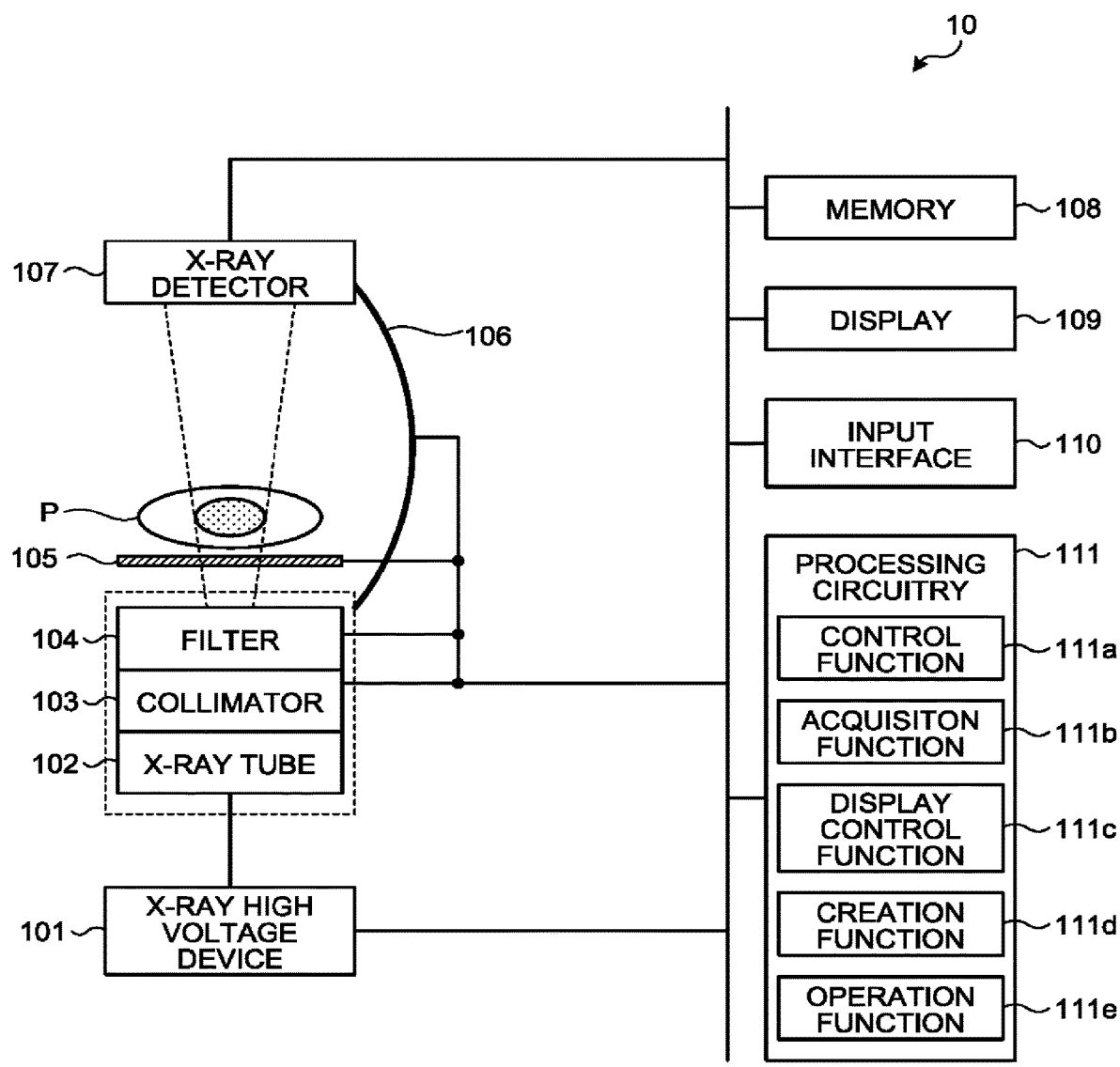
FIG. 11 is a block diagram illustrating a configuration example of an X-ray diagnostic apparatus according to a third embodiment.

In the embodiments described above, the medical information processing apparatus 30 includes the processing circuitry 34 including the creation function 34c and the operation function 34d. However, the embodiment is not limited thereto. For example, the processing circuitry 111 of the X-ray diagnostic apparatus 10 may have a function corresponding to the creation function 34c and the operation function 34d. For example, as illustrated in FIG. 11, the processing circuitry 111 may further include a creation function 111d corresponding to the creation function 34c and an operation function 111e corresponding to the operation function 34d. FIG. 11 is a block diagram illustrating a configuration example of the X-ray diagnostic apparatus 10 according to a third embodiment.

In this case, first, the acquisition function 111b acquires the three-dimensional medical image data or the three-dimensional image data. For example, the acquisition function 111b acquires the three-dimensional X-ray image data of the subject P as the three-dimensional medical image data. Next, the display control function 111c causes the display 109 to display the three-dimensional medical image data. The creation function 111d creates the figure indicating the movable region of the movable member of the X-ray diagnostic apparatus 10 based on the direction of the three-dimensional medical image data on the display 109. The display control function 111c causes the display 109 to further display the created figure indicating the movable region. In a case in which the processing circuitry 111 has the creation function 111d and the operation function 111e, the X-ray diagnostic system 1 does not necessarily include the medical information processing apparatus 30. Furthermore, the X-ray diagnostic system 1 may be constituted of only the X-ray diagnostic apparatus 10 without including the image storage apparatus 20.

The components of the devices according to the embodiments described above are merely conceptual, and it is not required that they are physically configured as illustrated necessarily. That is, specific forms of distribution and integration of the devices are not limited to those illustrated in the drawings. All or part thereof may be functionally or physically distributed/integrated in arbitrary units depending on various loads or usage states. Additionally, all or optional part of the processing functions executed by the respective devices may be implemented by a CPU and a computer program analyzed and executed by the CPU, or may be implemented as hardware based on wired logic.

The medical information processing method described above in the embodiments can be implemented by executing a medical information processing program prepared in advance with a computer such as a personal computer or a workstation. This medical information processing program can be distributed via a network such as the Internet. The medical information processing program is recorded in a computer-readable non-transitory recording medium such as a hard disk, a flexible disk (FD), a CD-ROM, an MO, and a DVD, and can be executed by being read out from the recording medium by the computer.

According to at least one of the embodiments described above, setting of the direction of X-rays to be emitted can be facilitated.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical information processing apparatus comprising:
processing circuitry configured to:
display a three-dimensional medical image on a display,
receive a rotation operation corresponding to rotating a direction of the three-dimensional medical image on the display,
in response to reception of the rotation operation, create a figure indicating, based on the direction of the three-dimensional medical image on the display before the rotation operation is executed, whether a movable member of an X-ray diagnostic apparatus is able to reach a position corresponding to the direction of the three-dimensional medical image after the rotation operation is executed, and
superimpose a display of the figure on the three-dimensional medical image on the display.

2. The medical information processing apparatus according to claim 1, wherein
the rotation operation corresponding to rotating the direction of the three-dimensional medical image on the display is an operation of rotating the direction of the three-dimensional medical image on the display based on a displacement of a pointer displayed on the display, and
the processing circuitry creates the figure so that a position of the pointer corresponds to a position indicated by the figure.

3. The medical information processing apparatus according to claim 2, wherein the processing circuitry is further configured to:
receive the rotating operation through an operation of designating a first position on the display and an operation of designating a displacement from the first position, and
create the figure so that the first position matches a position corresponding to the direction of the three-dimensional medical image before the rotation operation is executed.

4. The medical information processing apparatus according to claim 3, wherein the processing circuitry is further configured to create the figure so that a second position that is moved from the first position by the designated displacement matches a position corresponding to the direction of the three-dimensional medical image after the rotation operation is executed.

5. The medical information processing apparatus according to claim 1, wherein
the rotation operation corresponding to rotating the direction of the three-dimensional medical image on the display is an operation of rotating the direction of the three-dimensional medical image on the display based on a displacement of the position designated on the display, and
the processing circuitry is further configured to create the figure so that the designated position corresponds to a position indicated by the figure.

6. The medical information processing apparatus according to claim 5, wherein the processing circuitry is further configured to:
receive the rotating operation through the operation of designating a first position on the display and an operation of designating a displacement from the first position on the display, and
create the figure so that the first position matches a position corresponding to the direction of the three-dimensional medical image before the rotation operation is executed.

7. The medical information processing apparatus according to claim 6, wherein the processing circuitry is further configured to create the figure so that a second position that is moved from the first position by a designated displacement matches a position corresponding to the direction of the three-dimensional medical image after the rotation operation is executed.

8. The medical information processing apparatus according to claim 1, wherein the processing circuitry is further configured to:
acquire information about an arrangement of the X-ray diagnostic apparatus, and
create the figure further based on the information about the arrangement.

9. The medical information processing apparatus according to claim 8, wherein the processing circuitry is further configured to determine whether at least one of interference between configurations of the X-ray diagnostic apparatus and interference between one of the configurations of the X-ray diagnostic apparatus and a subject is caused based on the information about the arrangement, and create the figure.

10. The medical information processing apparatus according to claim 9, wherein
the X-ray diagnostic apparatus is a biplane apparatus including a first arm and a second arm, and
the processing circuitry is configured to determine whether interference between the first arm and the second arm is caused based on the information about the arrangement, and create the figure.

11. The medical information processing apparatus according to claim 9, wherein
the X-ray diagnostic apparatus is a biplane apparatus including a first arm, and a second arm configured to operate in synchronization with the first arm, and
the processing circuitry is further configured to determine, based on the information about the arrangement, when the first arm is rotated, whether at least one of a configuration other than the first arm and the second arm in the X-ray diagnostic apparatus and a subject interferes with the second arm that operates in synchronization with the first arm based on the information about the arrangement, and create the figure.

12. The medical information processing apparatus according to claim 1, wherein the processing circuitry is further configured to:
receive an operation of changing a display magnification of the three-dimensional medical image on the display, and
display the figure in a size corresponding to the display magnification.

13. The medical information processing apparatus according to claim 1, wherein the processing circuitry is further configured to display, as the figure, a figure in which a region that is reachable by the movable member and a region that is unreachable by the movable member are color-coded.

14. An X-ray diagnostic system comprising:
a movable member including an X-ray tube configured to generate X-rays and an X-ray detector configured to detect X-rays emitted from the X-ray tube and output a detection signal corresponding to an amount of the detected X-rays, the movable member being configured to control direction of the X-rays to be emitted with respect to a subject; and
the medical information processing apparatus of claim 1, wherein
the processing circuitry further acquires an X-ray image based on the detection signal.

15. A medical information processing method comprising:
displaying a three-dimensional medical image on a display;
receiving a rotation operation corresponding to rotating a direction of the three-dimensional medical image on the display that is input via an input interface;
in response to receiving the rotation operation, creating a figure indicating, based on the direction of the three-dimensional medical image on the display before the rotation operation is executed, whether a movable member of an X-ray diagnostic apparatus is able to reach a position corresponding to the direction of the three-dimensional medical image after the rotation operation is executed; and
superimposing a display of the figure on the three-dimensional medical image on the display.

16. A medical information processing apparatus comprising:
processing circuitry configured to:
display a three-dimensional medical image on a display, the three-dimensional medical image indicating a movable member of an X-ray diagnostic apparatus;
receive a rotation operation corresponding to rotating a direction of the three-dimensional medical image on the display;
create a figure indicating, based on the direction of the three-dimensional medical image on the display before the rotation operation is executed, whether the movable member of the X-ray diagnostic apparatus is able to reach a position corresponding to the direction of the three-dimensional medical image after the rotation operation is executed; and
superimpose a display of the figure on the three-dimensional medical image on the display.

* * * * *